(12) United States Patent
Kawai et al.

(10) Patent No.: US 12,303,342 B2
(45) Date of Patent: May 20, 2025

(54) LIQUID PROCESSING NOZZLE FOR PURIFYING LIQUID PIPING OF DENTAL DEVICE

(71) Applicants: Waseda Business Consulting Co., Ltd., Tokyo (JP); New Environmental Technology Council, Tokyo (JP)

(72) Inventors: Hiroyuki Kawai, Tokyo (JP); Masahiko Tanaka, Tokyo (JP)

(73) Assignees: WASEDA BUSINESS CONSULTING CO., LTD., Tokyo (JP); NEW ENVIRONMENTAL TECHNOLOGY COUNCIL, Tokyo (JP)

( * ) Notice: Subject to any disclaimer, the term of this patent is extended or adjusted under 35 U.S.C. 154(b) by 242 days.

(21) Appl. No.: 17/769,564

(22) PCT Filed: Sep. 30, 2020

(86) PCT No.: PCT/JP2020/037076
§ 371 (c)(1),
(2) Date: Apr. 15, 2022

(87) PCT Pub. No.: WO2021/075260
PCT Pub. Date: Apr. 22, 2021

(65) Prior Publication Data
US 2024/0122674 A1  Apr. 18, 2024

(30) Foreign Application Priority Data
Oct. 18, 2019  (JP) .................................. 2019-190685

(51) Int. Cl.
*A61C 1/00* (2006.01)
(52) U.S. Cl.
CPC .................................. *A61C 1/0076* (2013.01)

(58) Field of Classification Search
CPC ... A61C 1/0061; A61C 1/0069; A61C 1/0076; A61C 1/0084; A61C 1/0092
(Continued)

(56) References Cited

U.S. PATENT DOCUMENTS

2007/0031779 A1\* 2/2007 Tokui ................ B05C 17/00516
433/89
2018/0149284 A1\* 5/2018 Uchiyama ............... F16K 47/08

FOREIGN PATENT DOCUMENTS

CN      103025267 A  *  4/2013  ......... A61C 17/0202
CN      208710128 U  *  4/2019
(Continued)

OTHER PUBLICATIONS

International Search Report dated Nov. 17, 2020, issued in counterpart International Application No. PCT/JP2020/037076. (2 pages).
(Continued)

*Primary Examiner* — Matthew M Nelson
(74) *Attorney, Agent, or Firm* — WHDA, LLP

(57) ABSTRACT

A formation of a biofilm is suppressed in piping having a relatively small liquid flow rate. A liquid processing nozzle connected to a liquid piping between a handpiece and a water supply source piping includes a nozzle body in which a liquid inlet, a liquid outlet, and a liquid flow path communicating the liquid inlet and the liquid outlet are formed, and a plurality of protrusions protruding from an inner surface of the liquid flow path into the liquid flow path. The protrusions are arranged so that protrusion amounts from the inner surface of the liquid flow path into the liquid flow path gradually increase as they go from an upstream side to a downstream side of the liquid flow path in a liquid flow direction from the liquid inlet to the liquid outlet.

20 Claims, 24 Drawing Sheets

(58) Field of Classification Search
USPC .......................................................... 433/86
See application file for complete search history.

(56) References Cited

FOREIGN PATENT DOCUMENTS

| | | | | | |
|---|---|---|---|---|---|
| JP | 2015174055 A | * | 10/2015 | | |
| JP | 2018-75334 A | | 5/2018 | | |
| JP | 2018075334 A | * | 5/2018 | | |
| WO | WO-2016178436 A2 | * | 11/2016 | ................ | B01F 5/06 |
| WO | WO-2021075260 A1 | * | 4/2021 | ........... | A61C 1/0076 |

OTHER PUBLICATIONS

Extended (Supplementary)European Search Report dated Sep. 22, 2023, issued in counterpart EP Application No. 20876514.9. (5 pages).
Office Action dated Dec. 28, 2023, issued in counterpart TW application No. 109134028. (4 pages).

\* cited by examiner

LIQUID PROCESSING NOZZLE FOR PURIFYING LIQUID PIPING OF DENTAL DEVICE

TECHNICAL FIELD

The present invention relates to a liquid processing nozzle for purifying a liquid piping for supplying a liquid to a dental device.

BACKGROUND ART

Conventionally, in order to remove a biofilm formed in a piping for supplying tap water to a dental unit, there is a liquid processing nozzle attached to the piping and generating cavitation water (PTL 1). Cavitation is generated by screw members protruding into a liquid flow path of the liquid processing nozzle, thereby suppressing the formation of the biofilm in the piping. The liquid processing nozzle of PTL 1 is provided in a piping for supplying tap water to a dental unit provided with a handpiece and a gargle spittoon. The flow rate of tap water supplied to the handpiece is relatively small, from 0.04 liters per minute to 0.3 liters per minute, while the flow rate of tap water supplied to the gargle spittoon is relatively large, from 0.3 liters per minute to 2 liters per minute. In order to accommodate both flow rates, the liquid processing nozzle is connected to a piping having an inside diameter of about 10 mm to 15 mm which can supply tap water at a relatively high flow rate.

Therefore, since the inside diameter of a liquid inlet of the liquid processing nozzle can be made relatively large, the angle of a tapered portion from the liquid inlet to a restriction hole provided with the screw members can be made large. Thus, the flow velocity of the liquid is increased in the tapered portion, and cavitation can be generated by the screw members provided in the restriction hole.

CITATION LIST

Patent Literature

PTL 1: Japanese Patent Application Laid-Open No. 2018-75334.

SUMMARY OF INVENTION

Technical Problem

However, the piping connecting the dental unit and the dental device has a relatively small inside diameter of about 3 mm to 5 mm because the flow rate of the liquid is relatively small, from about 0.04 liters per minute to about 0.2 liters per minute. Therefore, in a case that the liquid processing nozzle is attached to the piping connecting the dental unit and the dental device, the inside diameter of the liquid inlet of the liquid processing nozzle is required to be small, so that the tapered portion for increasing the flow velocity of the liquid cannot be sufficiently formed. Therefore, sufficient cavitation may not be generated by the liquid processing nozzle.

It is therefore an object of the present invention to provide a liquid processing nozzle configured to suppress formation of a biofilm in piping even in a case where the liquid processing nozzle is connected to the piping having a relatively small liquid flow rate.

Solution to Problem

In order to solve the above problem, a liquid processing nozzle to be connected to a liquid piping between a handpiece and a water supply source piping according to an embodiment of the present invention comprises: a nozzle body in which a liquid inlet, a liquid outlet, and a liquid flow path communicating the liquid inlet and the liquid outlet are formed; and a plurality of protrusions protruding from an inner surface of the liquid flow path into the liquid flow path, wherein the plurality of protrusions are arranged so that protrusion amounts of the plurality of protrusions protruding from the inner surface of the liquid flow path into the liquid flow path gradually increase as they go from an upstream side to a downstream side of the liquid flow path in a flow direction of a liquid from the liquid inlet to the liquid outlet.

Advantageous Effects of Invention

According to the present invention, it is possible to provide a liquid processing nozzle configured to suppress formation of a biofilm in piping even in a case where the liquid processing nozzle is connected to the piping having a relatively small liquid flow rate.

DESCRIPTION OF EMBODIMENTS

The embodiments of the present invention will now be described with reference to the accompanying drawings.

First Embodiment (Dental Unit)

Figure 1:
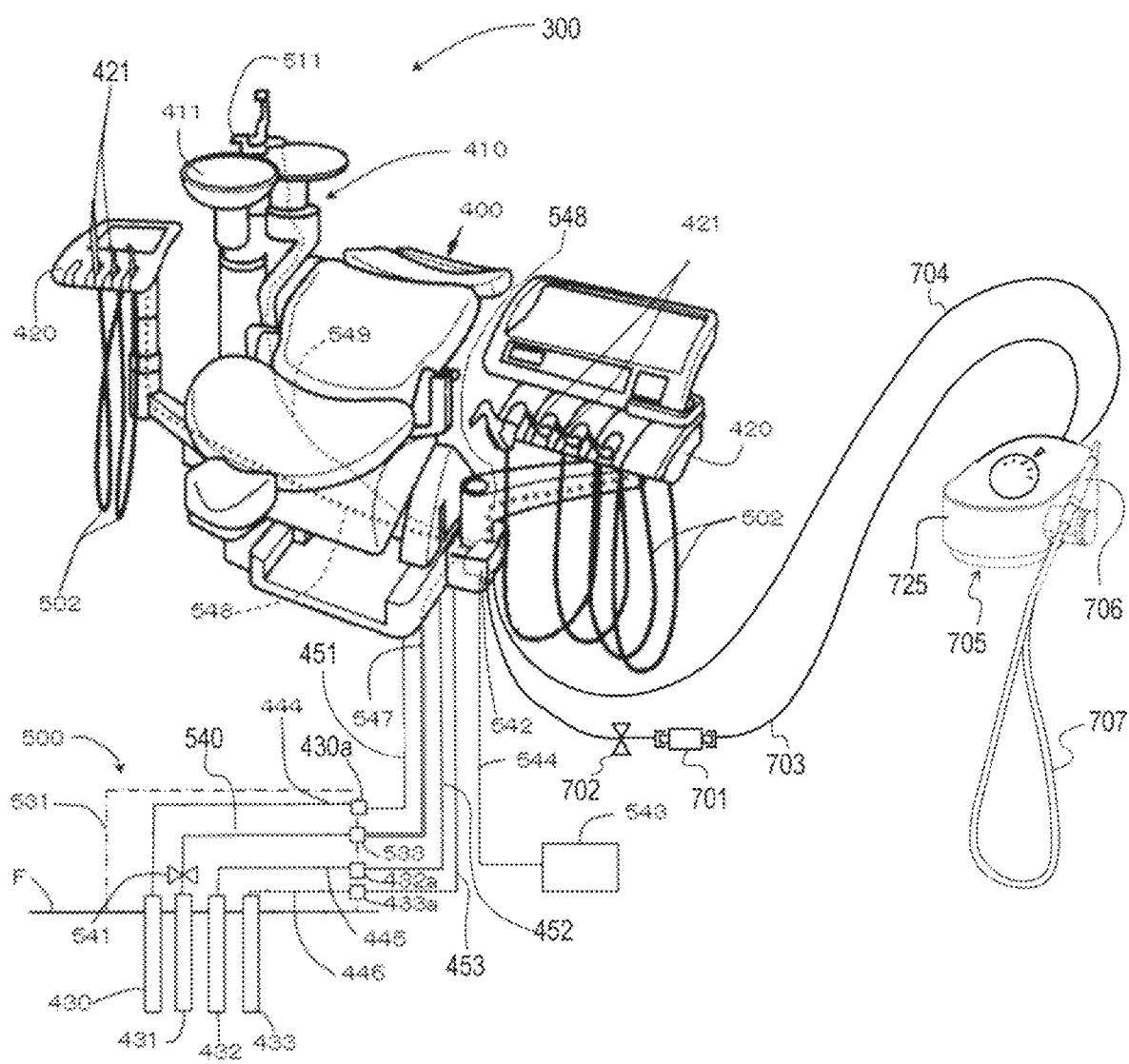
FIG. 1 is a view of a dental unit and an external device connected to the dental unit.

FIG. 1 shows a dental unit 300 and an external device (hereinafter referred to as a dental device) 705 connected to the dental unit 300. The dental unit 300 includes a dental treatment chair 400 installed on a floor surface F of a consultation room of a dental clinic, a unit body 410, and treatment tables 420. A gargle spittoon 411 having a discharge portion 511 for discharging washing water for gargle is provided on the upper portion of the unit body 410. The gargle spittoon 411 is disposed adjacent to the dental treatment chair 400 in a position in which a patient sitting on the dental treatment chair 400 can gargle.

The treatment tables 420 are provided with a plurality of handpieces 421 driven by air or electric power such as an engine handpiece, an ultrasonic scaler handpiece, a three-way syringe, and an air turbine handpiece. Each of the treatment tables 420 is arranged adjacent to the dental treatment chair 400 in a positional in which a dentist standing beside the dental treatment chair 400 can perform treatment operation to the patient. In the embodiment, the two treatment tables 420 are disposed on both sides of the dental treatment chair 400, respectively.

The handpiece 421 is switched between driving and non-driving by a switch provided on a body to be gripped by a hand or a foot pedal, and supplied with washing water through a water supply tube 502. The water supply tube 502 is a tube made of rubber or resin having an inside diameter of about 3 mm or more and 5 mm or less, and the passing flow rate of the washing water when the handpiece 421 is driven is about 0.03 liters or more per minute and 0.3 liters or less per minute. On the other hand, the discharge portion 511 of the gargle spittoon 411 is connected to a gargle washing water piping portion 549 having a water supply valve (not shown) driven by a switch or a sensor. The washing water of 0.5 liters or more per minute and 2 liters or less per minute is supplied to the discharge portion 511 through the gargle washing water piping portion 549.

The washing water supplied to the handpiece 421 and the discharge portion 511 is disinfection tap water having a free chlorine concentration of 0.1 ppm or more and 1 ppm or less (The washing water may be ozone disinfection tap water having a dissolved ozone concentration of 0.1 ppm or more and 1 ppm or less.). A distribution control box 542 is provided under the dental treatment chair 400. A handpiece piping portion 548 and the gargle washing water piping portion 549 are connected to the distribution control box 542. The distribution control box 542 is connected to a dental unit washing water supply device 500 through a plurality of pipes. The distribution control box 542 is connected to an air compressor 543 through an air supply source piping 544.

The dental unit washing water supply device 500 has a piping box (so-called a junction box) 531 attached to the dental treatment chair 400. The piping box 531 is fixed on the floor surface F below the dental treatment chair 400. The piping box 531 includes an electric wiring 444, a drain pipe 445, a suction piping 446, and a washing water main piping 540. One end of the electric wiring 444 is connected to a power source 430, and the other end of the electric wiring 444 is connected to a connector 430a of the piping box 531. The electric wiring 444 supplies electric power from the power source 430 to the electric drive unit of the dental treatment chair 400 through an electric wiring 451 connected to the connector 430a. One end of the drain pipe 445 is connected to a drain portion 432, and the other end is connected to a drain pipe joint 432a of the piping box 531. The drain pipe 445 drains the waste water from the gargle spittoon 411 to the drain portion 432 through a drain pipe 452 connected to the drain pipe joint 432a.

One end of the suction piping 446 is connected to a suction source 433, and the other end of the suction piping 446 is connected to a suction joint portion 433a of the piping box 531. The suction piping 446 is connected to a piping 453 for sucking in the oral cavity through the suction joint portion 433a. One end of the washing water main piping 540 is connected to a water supply source piping 431 through a water stop valve 541, and the other end of the washing water main piping 540 is connected to a washing water main piping 547 through a washing water joint 533 of the piping box 531. The washing water main piping 547 is connected to the distribution control box 542. The washing water main piping 547 supplies washing water to the handpiece piping portion 548 and the gargle washing water piping portion 549 through the distribution control box 542.

(Dental Device)

The dental device 705 has a drive portion 725, a handpiece 706 and a hose 707 for supplying washing water and electric power to the handpiece 706. The drive portion 725 of the dental device 705 is connected to the dental unit 300 by a washing water hose (liquid piping) 703 and an electric cord 704. The washing water hose 703 is connected to the water supply source piping 431 through the distribution control box 542 of the dental unit 300. However, the washing water hose 703 may be directly connected to the water supply source piping 431 without going through the distribution control box 542 of the dental unit 300. The electric cord 704 is connected to the power source 430 through the electric wiring 451, the connector 430a, and the electric wiring 444 of the dental unit 300.

The washing water hose 703 connecting the dental device 705 and the dental unit 300 is provided with a liquid processing nozzle 701. The liquid processing nozzle 701 is arranged in the vicinity of the distribution control box 542 of the dental unit 300. Between the liquid processing nozzle 701 and the distribution control box 542, a manual or electric water stop valve 702 is provided. If the water stop valve 541 for stopping the supply of the washing water from the water supply source piping 431 is provided, the water stop valve 702 is not necessarily provided. In a case that the washing water hose 703 is directly connected to the water supply source piping 431, the liquid processing nozzle 701 may be directly connected to the water supply source piping 431, and the washing water hose 703 may be connected to the liquid processing nozzle 701.

(Liquid Processing Nozzle)

Figure 2:
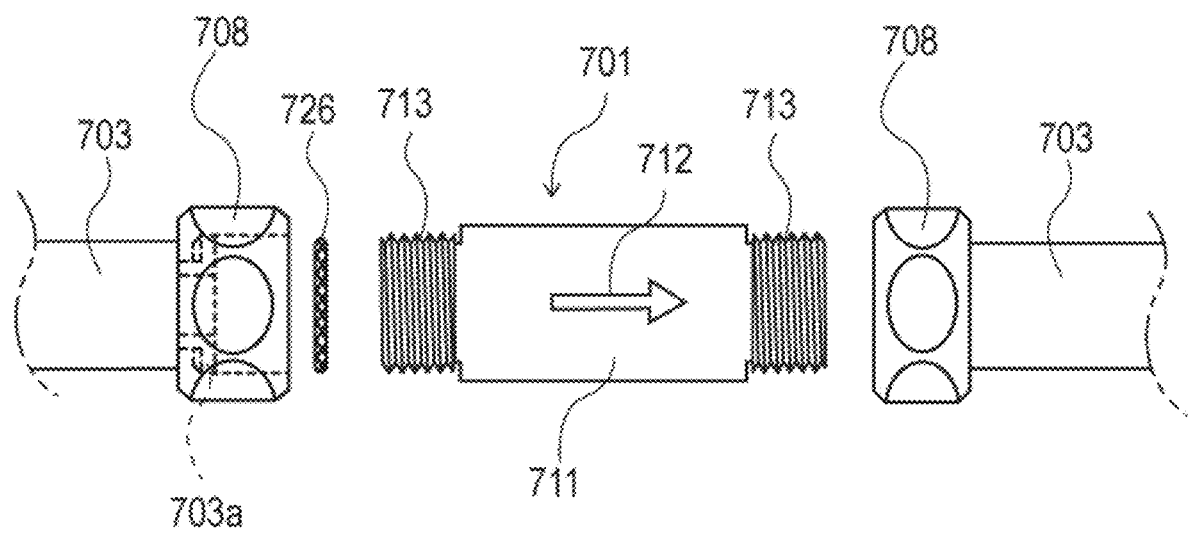
FIG. 2 is a view of a liquid processing nozzle connected to a washing water hose.

The liquid processing nozzle 701 will be described below. FIG. 2 is a view showing the liquid processing nozzle 701 connected to the washing water hose 703. Union screws 713 are formed at both ends of the liquid processing nozzle 701. A union flange 703a is formed at an end of the washing water hose 703. A union nut 708 is attached to the union flange 703a. The union screw 713, the union flange 703a and the union nut 708 constitute a union joint for connecting the liquid processing nozzle 701 to the washing water hose 703 without rotating the washing water hose 703. The liquid processing nozzle 701 is connected to the washing water hose 703 by the union joint by screwing the union nut 708 onto the union screw 713. A cover 711 of the liquid processing nozzle 701 is provided with a mark 712 indicating a flow direction of the washing water. The mark 712 indicates a direction of attachment of the liquid processing nozzle 701 with respect to the flow of the washing water.

A filter 726 is provided upstream of the liquid processing nozzle 701 in the flow direction of the washing water indicated by the mark 712. In the embodiment, the filter 726 is a wire mesh made of stainless steel. The filter 726 may be, for example, a mesh made of resin. The filter 726 can collect debris. The liquid processing nozzle 701 is easily attachable to and detachable from the washing water hose 703 by the union joint. Therefore, for example, in a case that the liquid processing nozzle 701 is clogged, the water stop valve 702 is closed and the liquid processing nozzle 701 is removed from the washing water hose 703. The filter 726 is removed to remove debris. The clogging can be eliminated by passing air or water through the liquid processing nozzle 701 in the direction opposite to the flow direction of the liquid. Thereafter, the filter 726 is attached, and the liquid processing nozzle 701 can be easily attached to the washing water hose 703 by the union joint.

Figure 3:
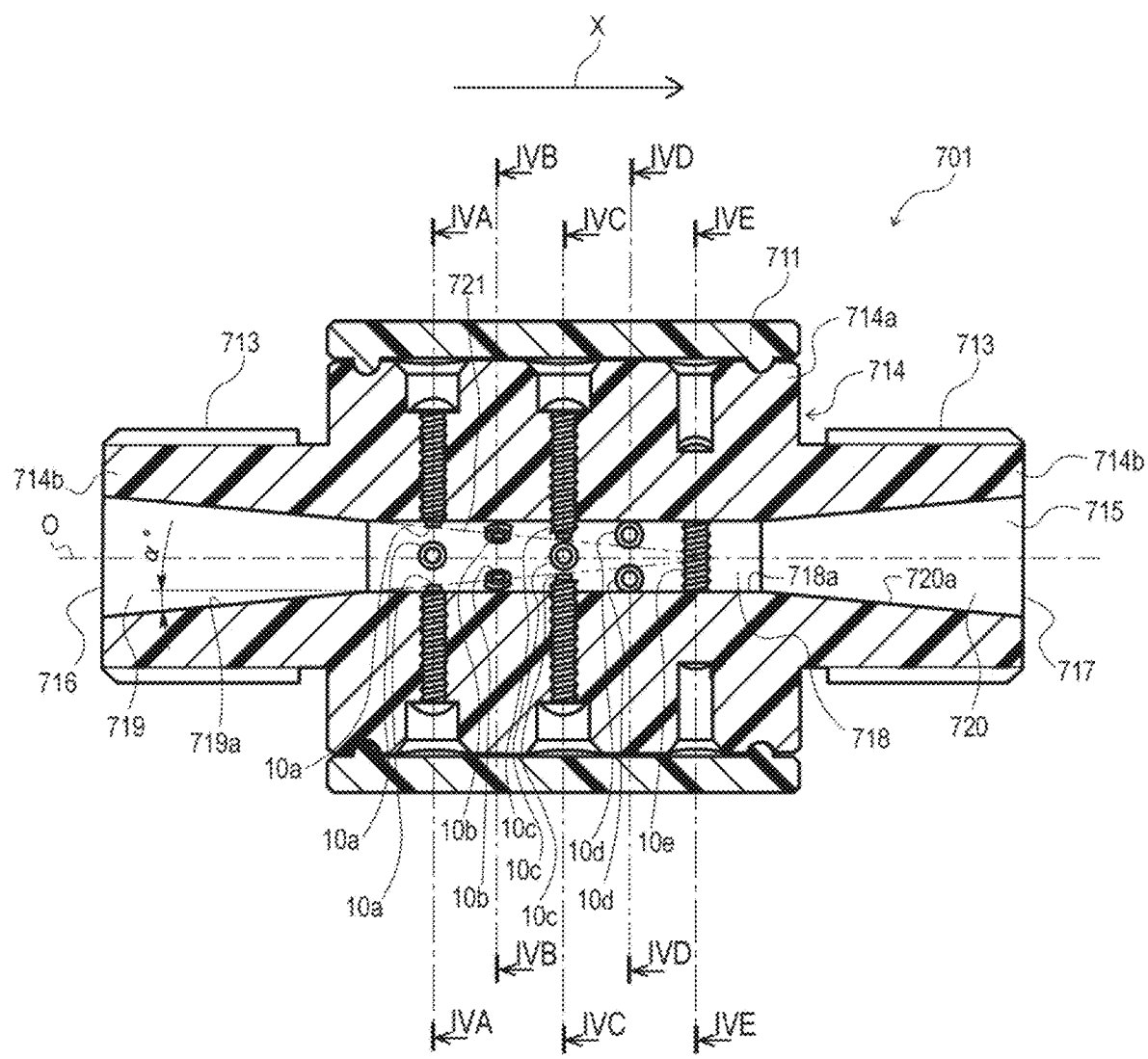
FIG. 3 is a cross-sectional view of the liquid processing nozzle of a first embodiment.

FIG. 3 is a cross-sectional view of the liquid processing nozzle 701 of the first embodiment. The arrow X indicates the flow direction of the liquid. The liquid processing nozzle 701 includes a nozzle body 714 and the cover 711 covering the nozzle body 714. The nozzle body 714 includes a cylindrical large diameter portion 714a and cylindrical small-diameter portions 714b on both sides of the large diameter portion 714a. The cover 711 is attached to the large diameter portion 714a. The union screws 713 are formed on the small diameter portions 714b. A liquid flow path 715 having a circular cross section is formed along the center axis O through the nozzle body 714. The liquid flow path 715 has a liquid inlet 716 at an upstream end (one end on the left side in FIG. 3) in the flow direction X and a liquid outlet 717 at a downstream end (the other end on the right side in FIG. 3) in the flow direction X. The liquid flow path 715 communicates the liquid inlet 716 with the liquid outlet 717.

A restriction hole 718 of which a circular cross-section has a smaller diameter than the diameters of the liquid inlet 716 and the liquid outlet 717 is formed at an intermediate position of the liquid flow path 715 in the flow direction X. The cross-sectional area of the restriction hole 718 is smaller than the area of the liquid inlet 716. The liquid flow path 715 from the liquid inlet 716 to the restriction hole 718 forms an inflow chamber 719. The liquid flow path 715 from the restriction hole 718 to the liquid outlet 717 forms an outflow chamber 720.

The nozzle body 714 and the cover 711 are made of a resin material such as ABS (acrylonitrile butadiene styrene), nylon, polycarbonate, polyacetal, PTFE (polytetrafluoroethylene), and DURACON (trademark). However, the nozzle body 714 and the cover 711 may be made of, for example, a metal such as stainless steel or brass, or a ceramic such as alumina.

The total length of the liquid processing nozzle 701 is, for example, 20 mm or more and 60 mm or less. The outside diameter of the liquid processing nozzle 701 is, for example, 10 mm or more and 35 mm or less. The washing water hose 703 is made of a material such as rubber or resin and has an inside diameter of about 3 mm or more and 8 mm or less. Inside diameters of the liquid inlet 716 and the liquid outlet 717 of the liquid processing nozzle 701 are substantially the same as the inside diameter of the washing water hose 703. An inside diameter of the restriction hole 718 is, for example, 2 mm or more and 3 mm or less. The inflow chamber 719 has a converged surface (hereinafter referred to as a tapered surface) 719a from the liquid inlet 716 to the restriction hole 718. Similarly, the outflow chamber 720 has a tapered surface 720a from the liquid outlet 717 to the restriction hole 718. The inclination angles $\alpha$ of the tapered surfaces 719a and 720a of the inflow chamber 719 and the outflow chamber 720 are, for example, 0° or more and 12° or less. An aspect ratio of the restriction hole 718 of the embodiment is 4 or more and 6 or less. However, the aspect ratio of the restriction hole 718 is not limited to this, and may be smaller than 4 or larger than 6.

A plurality of protrusions 10a, 10b, 10c, 10d, and 10e are provided on an inner surface 718a of the restriction hole 718. The plurality of protrusions 10a, 10b, 10c, 10d, and 10e are arranged such that the respective most protruding portions of the plurality of protrusions 10a, 10b, 10c, 10d, and 10e protruding from the inner surface 718a of the restriction hole 718 are positioned on a virtual extension surface 721 extended from the tapered surface 719a of the inflow chamber 719 in the flow direction X within a predetermined allowable value of about ±0.1 mm. The liquid processing nozzle 701 of the embodiment is attached to the washing water hose 703 having a small inside diameter and a small liquid flow rate. Even if the tapered surface 719a is tapered from the inside diameter of the liquid inlet 716 corresponding to the inside diameter of the washing water hose 703 to the inside diameter of the restriction hole 718, the inclination angle $\alpha$ of the tapered surface 719a of the inflow chamber 719 is small, and thus there is a concern that a sufficient depressurization effect of the flowing liquid cannot be obtained. If the inclination angle $\alpha$ of the tapered surface 719a of the inflow chamber 719 is sufficiently secured, the inside diameter of the restriction hole 718 may become too small to secure a sufficient flow rate. Therefore, in order to exhibit the same decompression effect as that of the tapered surface 719a while securing the inside diameter of the restriction hole 718 to a sufficient size, tips of the plurality of protrusions 10a, 10b, 10c, 10d, and 10e are arranged on the virtual extension surface 721. With this arrangement, a flow velocity of the liquid passing through the restriction hole 718 can be increased while securing the flow rate of the liquid.

Figure 4A:
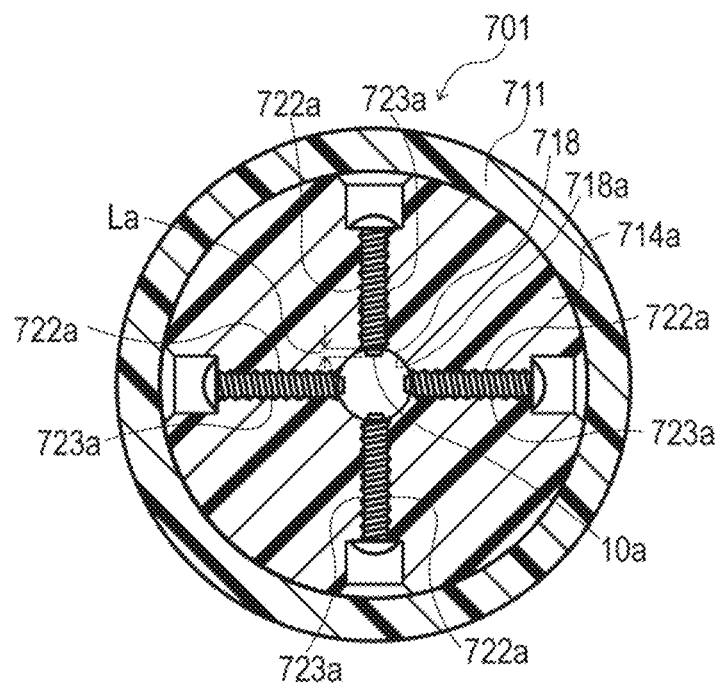
FIG. 4A is a cross-sectional view of the liquid processing nozzle taken along the lines IVA-IVA of FIG. 3.

FIG. 4A, FIG. 4B, FIG. 4C, FIG. 4D, and FIG. 4E are cross-sectional views of the liquid processing nozzle 701 of the first embodiment. In the embodiment, the plurality of protrusions 10a, 10b, 10c, 10d, and 10e are constituted by a plurality of screw members 723a, 723b, 723c, 723d, and 723e, respectively. FIG. 4A is a cross-sectional view taken along the lines IVA-IVA of FIG. 3. In the large diameter portion 714a, four screw holes 722a penetrating from an outer peripheral surface of the large diameter portion 714a to the restriction hole 718 are formed at intervals of approximately 90 degrees. The screw members 723a are screwed into the screw holes 722a. The tip ends of the screw members 723a constitute the protrusions 10a. The screw tips or the most protruding portions of the screw members 723a are away from the inner surface 718a of the restriction hole 718 by a distance La. The distance La is a protrusion amount of the screw members 723a. In a projection of the liquid flow path 715 of the nozzle body 714 onto a plane orthogonal to the center axis O, the four protrusions 10a are arranged in a cross shape surrounding the center axis O, and a liquid flow gap is formed at the center position of the cross formed by the four protrusions 10a.

Figure 4B:
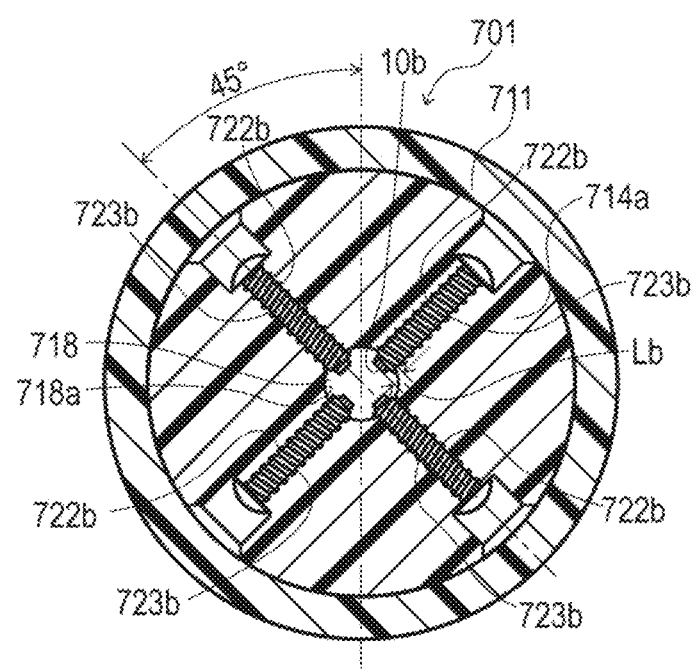
FIG. 4B is a cross-sectional view of the liquid processing nozzle taken along the lines IVB-IVB of FIG. 3.

FIG. 4B is a cross-sectional view taken along the lines IVB-IVB of FIG. 3. In the large diameter portion 714a, four screw holes 722b penetrating from the outer peripheral surface of the large diameter portion 714a to the restriction hole 718 are formed at intervals of approximately 90 degrees. The screw holes 722a shown in FIG. 4A and the screw holes 722b shown in FIG. 4B are shifted by approximately 45 degrees. The screw members 723b are screwed into the screw holes 722b. The tip ends of the screw members 723b constitute the protrusions 10b. The screw tips or the most protruding portions of the screw members 723b are away from the inner surface 718a of the restriction hole 718 by a distance Lb. The distance Lb is a protrusion amount of the screw members 723b. The four protrusions 10a (first set) are disposed upstream of the four protrusions 10b (second set) in the flow direction X. The distance Lb is larger than the distance La.

In the projection to the plane orthogonal to the center axis O of the liquid flow path 715 of the nozzle body 714, the four protrusions 10b are arranged in a cross shape surrounding the center axis O, and a liquid flow gap is formed at the center position of the cross formed by the four protrusions 10b. The set of the four screw members 723a and the set of the four screw members 723b incorporated in the restriction hole 718 are arranged at positions shifted from each other in a direction (flow direction X) along the center axis O.

Figure 4C:
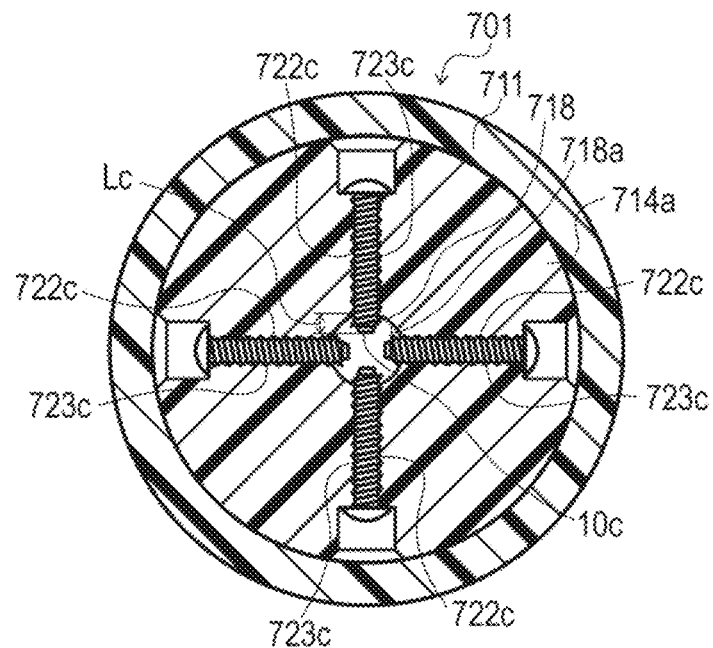
FIG. 4C is a cross-sectional view of the liquid processing nozzle taken along the lines IVC-IVC of FIG. 3.

FIG. 4C is a cross-sectional view taken along the lines IVC-IVC of FIG. 3. In the large diameter portion 714a, four screw holes 722c penetrating from the outer peripheral surface of the large diameter portion 714a to the restriction hole 718 are formed at intervals of approximately 90 degrees. When viewed along the center axis O shown in FIG. 3, the screw holes 722a shown in FIG. 4A and the screw holes 722c shown in FIG. 4C are substantially overlapped each other. The screw members 723c are screwed into the screw holes 722c. The tip ends of the screw members 723c constitute the protrusions 10c. The screw tips or the most protruding portions of the screw members 723c are away from the inner surface 718a of the restriction hole 718 by a distance Lc. The distance Lc is a protrusion amount of the screw members 723c. The distance Lc is larger than the distance Lb.

In the projection to the plane orthogonal to the center axis O of the liquid flow path 715 of the nozzle body 714, the four protrusions 10c are arranged in a cross shape surrounding the center axis O, and a liquid flow gap is formed at the center position of the cross formed by the four protrusions 10c. The set of four screw members 723b and the set of four screw members 723c incorporated in the restriction hole 718 are arranged at positions shifted from each other in the direction (flow direction X) along the center axis O.

Figure 4D:
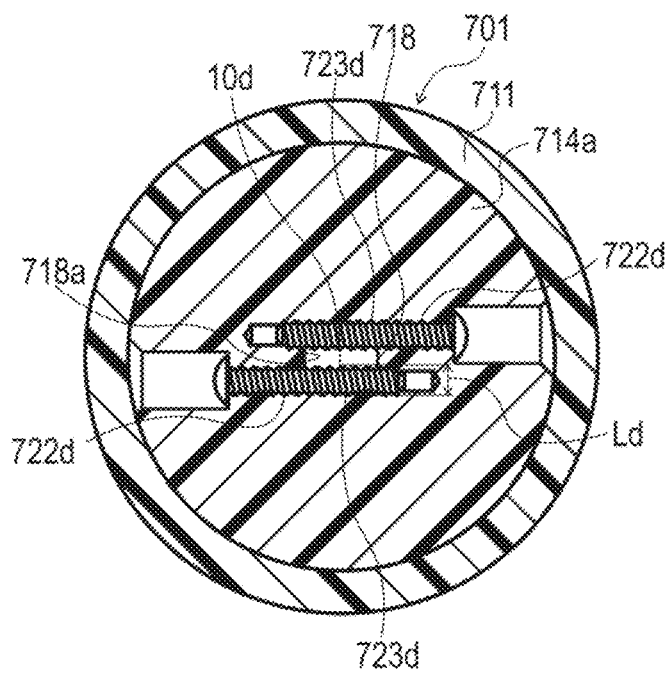
FIG. 4D is a cross-sectional view of the liquid processing nozzle taken along the lines IVD-IVD of FIG. 3.

FIG. 4D is a cross-sectional view taken along the lines IVD-IVD of FIG. 3. In the large diameter portion 714a, two screw holes 722d penetrating from the outer peripheral surface of the large diameter portion 714a to the restriction hole 718 are formed in opposite directions. The directions of the two screw holes 722d are different by about 180 degrees. The screw members 723d are screwed into the screw holes 722d. The most protruding portions of the screw members 723d protruding from the inner surface 718a of the restriction hole 718 are not the tip ends of the screw members 723d but screw shaft parts (bellies of the screws). The screw shaft parts of the screw members 723d are arranged so as to be parallel to each other across the center axis O of the liquid flow path 715. A liquid flow gap is formed between the two parallel screw members 723d. The most protruding portions of the screw shaft parts of the screw members 723d constitute the protrusions 10d. The most protruding screw shaft parts of the screw members 723d are away from the inner surface 718a of the restriction hole 718 by a distance Ld. The distance Ld is a protrusion amount of the screw members 723d. The distance Ld is larger than the distance Lc.

Figure 4E:
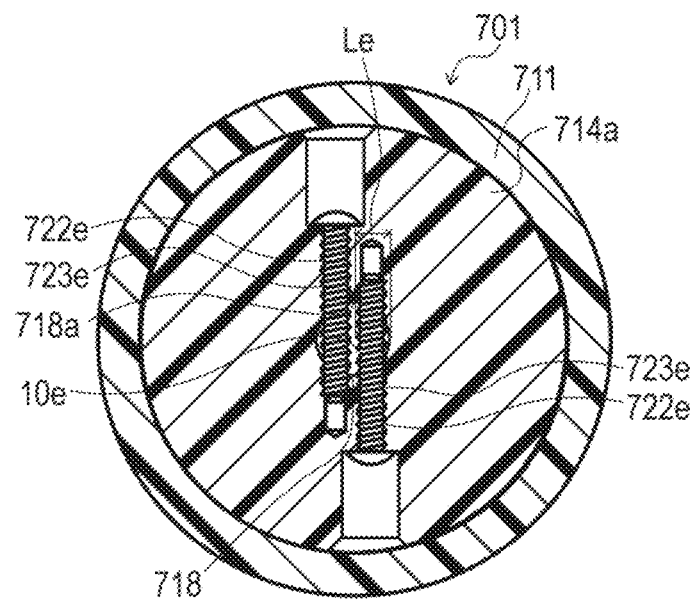
FIG. 4E is a cross-sectional view of the liquid processing nozzle taken along the lines IVE-IVE of FIG. 3.

FIG. 4E is a cross-sectional view taken along the lines IVE-IVE of FIG. 3. In the large diameter portion 714a, two screw holes 722e penetrating from the outer peripheral surface of the large diameter portion 714a to the restriction hole 718 are formed in opposite directions. The directions of the two screw holes 722e are different by approximately 180 degrees. The screw holes 722d shown in FIG. 4D and the screw holes 722e shown in FIG. 4E are shifted by approximately 90 degrees. The screw members 723e are screwed into the screw holes 722e. The most protruding portions of the screw members 723e protruding from the inner surface 718a of the restriction hole 718 are not the tip ends of the screw members 723e but screw shaft parts. The screw shaft parts of the screw members 723e are arranged so as to be parallel to each other across the center axis O of the liquid flow path 715. A liquid flow gap is formed between the two parallel screw members 723e. The most protruding portions of the screw shaft parts of the screw members 723e constitute the protrusions 10e. The most protruding portions of the screw shaft parts of the screw members 723e are away from the inner surface 718a of the restriction hole 718 by a distance Le. The distance Le is a protrusion amount of the screw members 723e. The distance Le is larger than the distance Ld.

When the two screw members 723d shown in FIG. 4D and the two screw members 723e shown in FIG. 4E are projected onto the plane orthogonal to the center axis O of the liquid flow path 715 of the nozzle body 714, a parallel-cross shape (hash mark) is obtained. It is preferable that the center of the parallel-cross shape is on the center axis O.

The distances La, Lb, Lc, Ld, and Le by which the protrusions 10a, 10b, 10c, 10d, and 10e protrude from the inner surface 718a of the restriction hole 718 have the following relationship.

$$La < Lb < Lc < Ld < Le$$

As the protrusions 10a, 10b, 10c, 10d, and 10e go from upstream to downstream in the liquid flow direction X, the distances La, Lb, Lc, Ld, and Le protruding from the inner surface 718a of the restriction hole 718 gradually increase. In this way, the virtual curved surface connecting the most protruding portions of the protrusions 10a, 10b, 10c, 10d, and 10e is tapered from the upstream to the downstream in the liquid flow direction X. Thus, the flow velocity of the liquid passing through the restriction hole 718 is further increased, and the possibility of generating cavitation in the liquid by the protrusions 10a, 10b, 10c, 10d and 10e can be increased.

The screw members 723a, 723b, 723c, 723d, and 723e are made of a material such as stainless steel, carbon steel, aluminum alloy, copper alloy or resin. The screw members 723a, 723b, 723c, 723d, and 723e may be made of a corrosion-resistant material such as titanium alloy, a heat-resistant material such as HASTELLOY (trademark) or INCONEL (trademark), or an abrasion-resistant ceramic material such as quartz or alumina.

The screw members 723a, 723b, 723c, 723d, and 723e constitute the protrusions 10a, 10b, 10c, 10d, and 10e have one screw thread formed in a spiral shape. The protrusions 10a, 10b, 10c, 10d, and 10e may have a plurality of threads formed in the spiral shape. The protrusions 10a, 10b, 10c, 10d, and 10e are preferably provided with a ridge part and a groove part. The ridge part and the groove part may not be integrated in the spiral shape. The ridge parts and the groove parts may be formed by a plurality of circumferentially closed portions closely arranged in the axial direction of the protrusions 10a, 10b, 10c, 10d, and 10e. The protrusion 10 may be provided with a plurality of ridge parts and a plurality of groove parts in which the ridge part and the groove part are alternately arranged in the axial direction of the protrusion 10.

Figure 5:
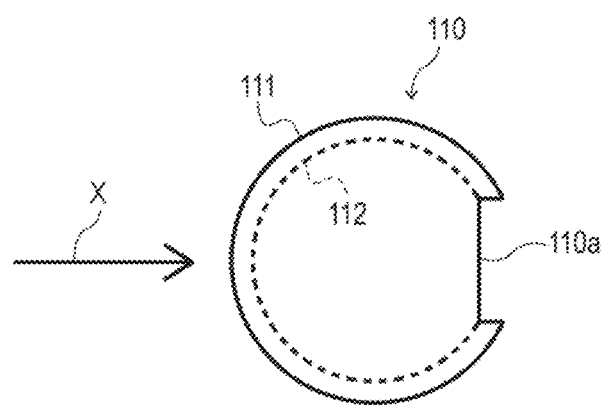
FIG. 5 is an enlarged cross-sectional view of a protrusion of a modification example.

Further, the ridge part and the groove part are not necessary to be formed over the entire circumference in the circumferential direction of the protrusions 10a, 10b, 10c, 10d, and 10e, but they may be formed in part. FIG. 5 is an enlarged cross-sectional view of a protrusion 110 of a modification example. As shown in FIG. 5, a notch part 110a extending in the axial direction of the protrusion 110 may be formed in a surface on the downstream side of the protrusion 110 in the flow direction X where the function as a cavitation point is unlikely to be exhibited. The ridge part 111 and the groove part 112 of the protrusion 110 may be cut in a portion in the circumferential direction by the notch part 110a.

When the distance Lc of the protrusions 10c is increased, the protrusions 10c come into contact with each other, but it is only necessary to form the liquid flow gap at the center of the cross formed by the four protrusions 10c. For example, the protrusions 10c may be shifted from each other in the flow direction X so as not to contact each other so that the distance Lc of the protrusions 10c can be increased. However, if the liquid flow gap is not formed at the central position, the release and cleaning effect of the biofilm adhered to the inner wall of the washing water hose 703 are reduced. Therefore, it is preferable to set the distance Lc of the protrusions 10c so that the liquid flow gap is formed at the center position of the cross formed by the four protrusions 10c.

In the embodiment, the protrusions 10a, 10b, 10c, 10d, and 10e are formed of the screw members 723a, 723b, 723c, 723d, and 723e. However, the protrusions 10a, 10b, 10c, 10d, and 10e may be formed integrally with the nozzle body 714. The protrusions 10a, 10b, 10c, 10d, and 10e may have a cylindrical shape without grooves. Alternatively, the protrusions 10a, 10b, 10c, 10d and 10e may have a polygonal shape having a triangular, quadrilateral, pentagonal, hexagonal or other polygonal cross section. In the embodiment, the five sets of protrusions 10a, 10b, 10c, 10d, and 10e are provided. However, the number of sets of protrusions is not limited to the five sets, but may be three or four sets, or six or more sets of protrusions may be provided.

The liquid processing nozzle 701 is provided with a type (type A) in which the screw tips of the screw members 723a, 723b, and 723c face the center axis O in a cross section taken along the plane orthogonal to the center axis O of the liquid flow path 715, and a type (type B) in which the screw shaft parts of the screw members 723d and 723e are closest to the center axis O. In the embodiment, the type A is disposed upstream of the type B in the flow direction X. However, the embodiment is not limited to this, and the type A may be disposed downstream of the type B in the flow direction X. Further, the type A and the type B may be alternately arranged in the order of, for example, the type A, the type B, the type A, the type B, and the type A from the upstream side to the downstream side in the flow direction X.

According to the embodiment, even in a case that the liquid processing nozzle 701 is connected to the washing water hose 703 having the relatively small liquid flow rate, the formation of the biofilm in the washing water hose 703 can be suppressed.

(Experiments Using a Liquid Processing Nozzle 701)

An experiment using the liquid processing nozzle 701 will be described below. The usage environment of the liquid processing nozzle 701 is shown in Table 1.

TABLE 1

| | Liquid Processing Nozzle 701 |
|---|---|
| Scope | Scaler, etc. |
| Attaching Place | Unit Outside |
| Hose Diameter | Inside Diameter 4 mm/Outside Diameter 6 mm |
| Water Flow Rate | 50 milliliters per minute |

Experiment 1

1-1 Contents of Experiment

Figure 6:
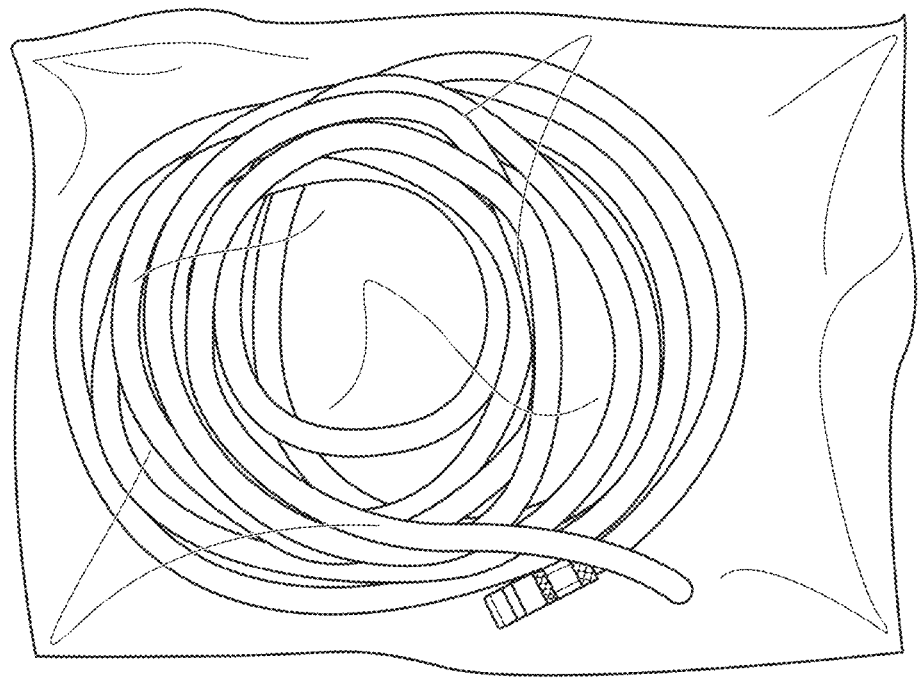
FIG. 6 is a view showing a photograph of a hose actually used in a dental clinic.

FIG. 6 is a view showing a photograph of a hose actually used in a dental clinic. As a demonstration experiment, the hose actually used in the dental clinic shown in FIG. 6 is used. The dirt discharged and the residue after passing water for a fixed time are compared between the one where tap water is flowed in a hose to which the liquid processing nozzle 701 is attached and the one where tap water is flowed in a hose to which the liquid processing nozzle 701 is not attached.

Figure 7:
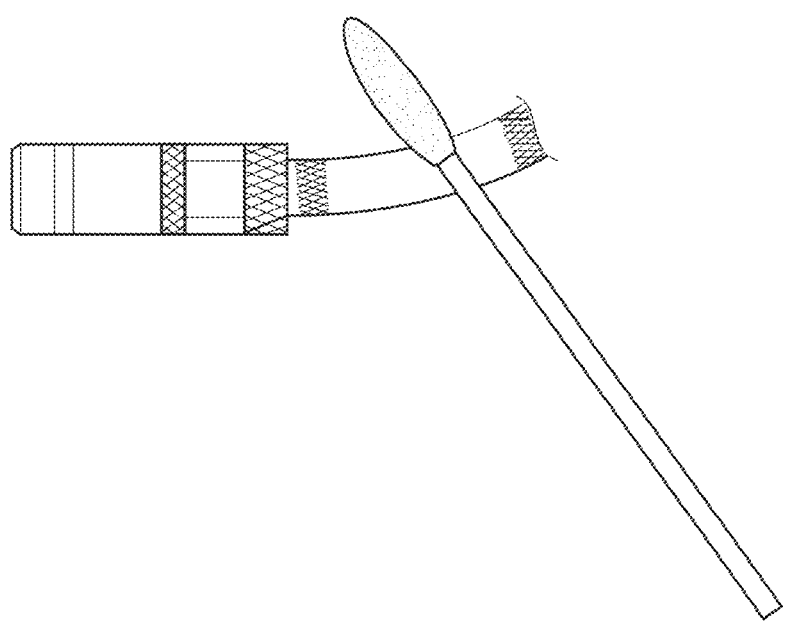
FIG. 7 is a view showing a photograph of a cotton swab through a metal joint side end of the hose.
Figure 8:
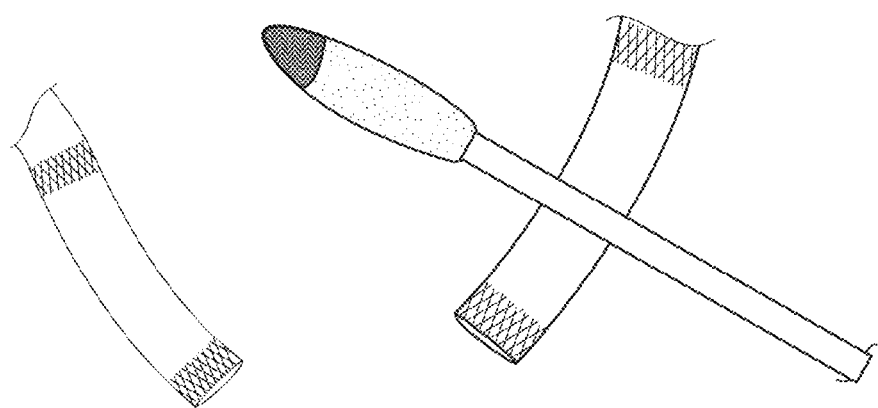
FIG. 8 is a view showing a photograph of a cotton swab through an opposite side end of the hose.

A metal joint side end and an opposite side end were cut 30 mm, and the situation of the hose inner walls were confirmed through cotton swabs. FIG. 7 is a view showing a photograph of a cotton swab inserted through the metal joint side end of the hose. FIG. 8 is a view showing a photograph of a cotton swab inserted through the opposite side end of the hose. Dark yellow contamination was observed on the metal joint side end (FIG. 7), and black contamination was observed on the opposite side end (FIG. 8). From the color difference, it is assumed that the metal joint side end has biofilm formation by bacteria, and the opposite side end has adhesion of fungus such as black mold.

1-2 Experimental Protocols

Two hoses having a length of 100 mm are cut from the hose end contaminated with black inside (on the side opposite to the metal joint side), and nanobubble water generated by the liquid processing nozzle 701 is made to flow into one hose 21, and tap water is made to flow into the other hose 22 (comparison object). Water temperature is 35° C. The flow rate was set at 50 milliliters per minute for both nanobubble water and tap water. Since the hoses 21 and 22 are not transparent, water was passed for a fixed period of time, and the states of dirt discharged from the hoses 21 and 22 were visually confirmed. When the amount of dirt being drained had decreased, the water was stopped and the hose was opened to check the inside.

1-3 Experimental Results

Figure 9:
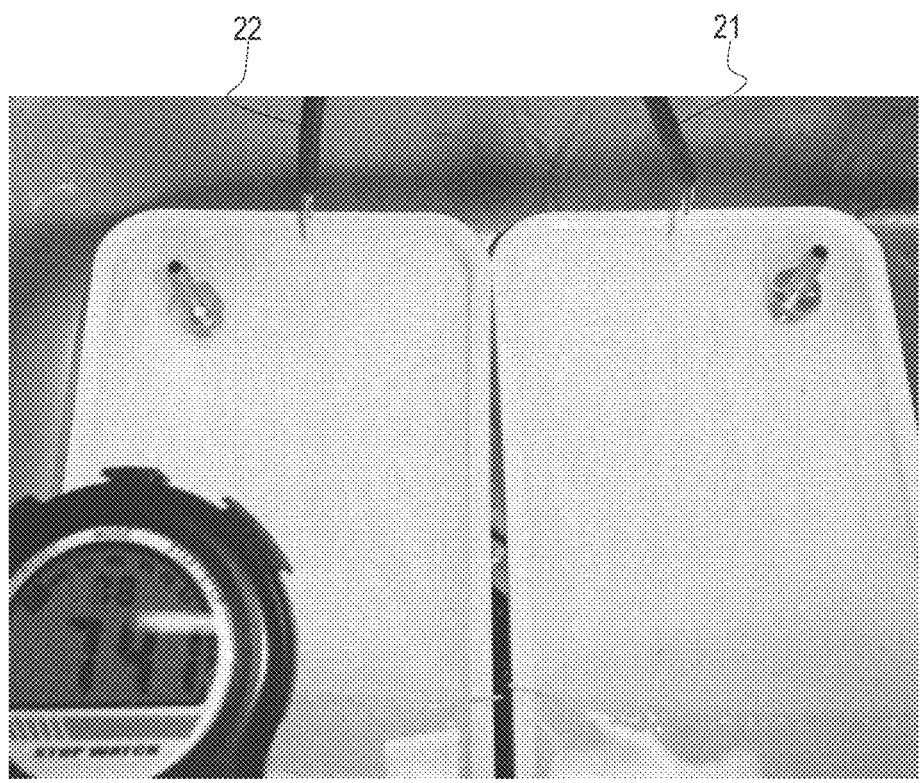
FIG. 9 is a view showing a photograph of dirt discharged from the hoses after 7 minutes.
Figure 10:
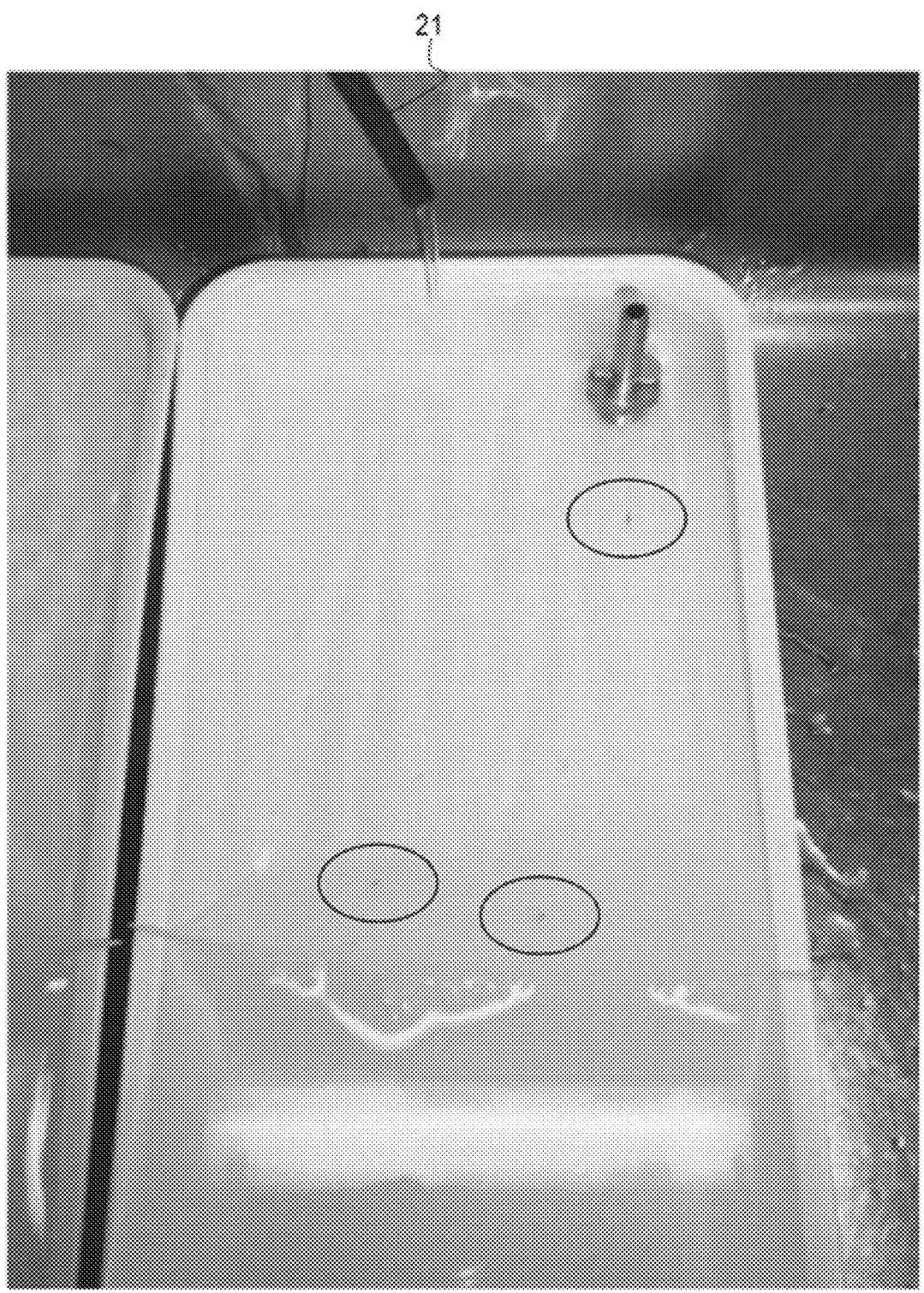
FIG. 10 is an enlarged view of a photograph of dirt discharged from the hose using the liquid processing nozzle.

FIG. 9 is a view showing a photograph of dirt discharged from the hoses 21 and 22 after 7 minutes. The left side of FIG. 9 is the hose 22 through which tap water is passed, and the right side of FIG. 9 is the hose 21 using the liquid processing nozzle 701. FIG. 10 is an enlarged view of a photograph of dirt discharged from the hose 21 using the liquid processing nozzle 701. After a lapse of 7 minutes from the start of water flow, black dot shaped fragments flowed out of only the hose 21 using the liquid processing nozzle 701, and the water-resistant paper captured them. However, no particular effluent was seen from the hose 22 through which tap water passed.

Figure 11:
FIG. 11 is a view showing a photograph of dirt discharged from the hoses after 11 minutes.

FIG. 11 is a view showing a photograph of dirt discharged from the hoses 21 and 22 after 11 minutes. The left side in FIG. 11 is the hose 22 through which tap water is passed, and the right side in FIG. 11 is the hose 21 using the liquid processing nozzle 701. As can be seen from FIG. 11, after 11 minutes, it was confirmed that black dot shaped fragments and fine algae shaped dirt were discharged only from the hose 21 using the liquid processing nozzle 701. It was confirmed that no dirt was discharged from the hose 22 which was supplied with tap water without using the liquid processing nozzle 701. After that, there was no change between 20 minutes and 30 minutes after the start of water flow, and water flow was stopped when 30 minutes had been lapsed.

Figure 12:
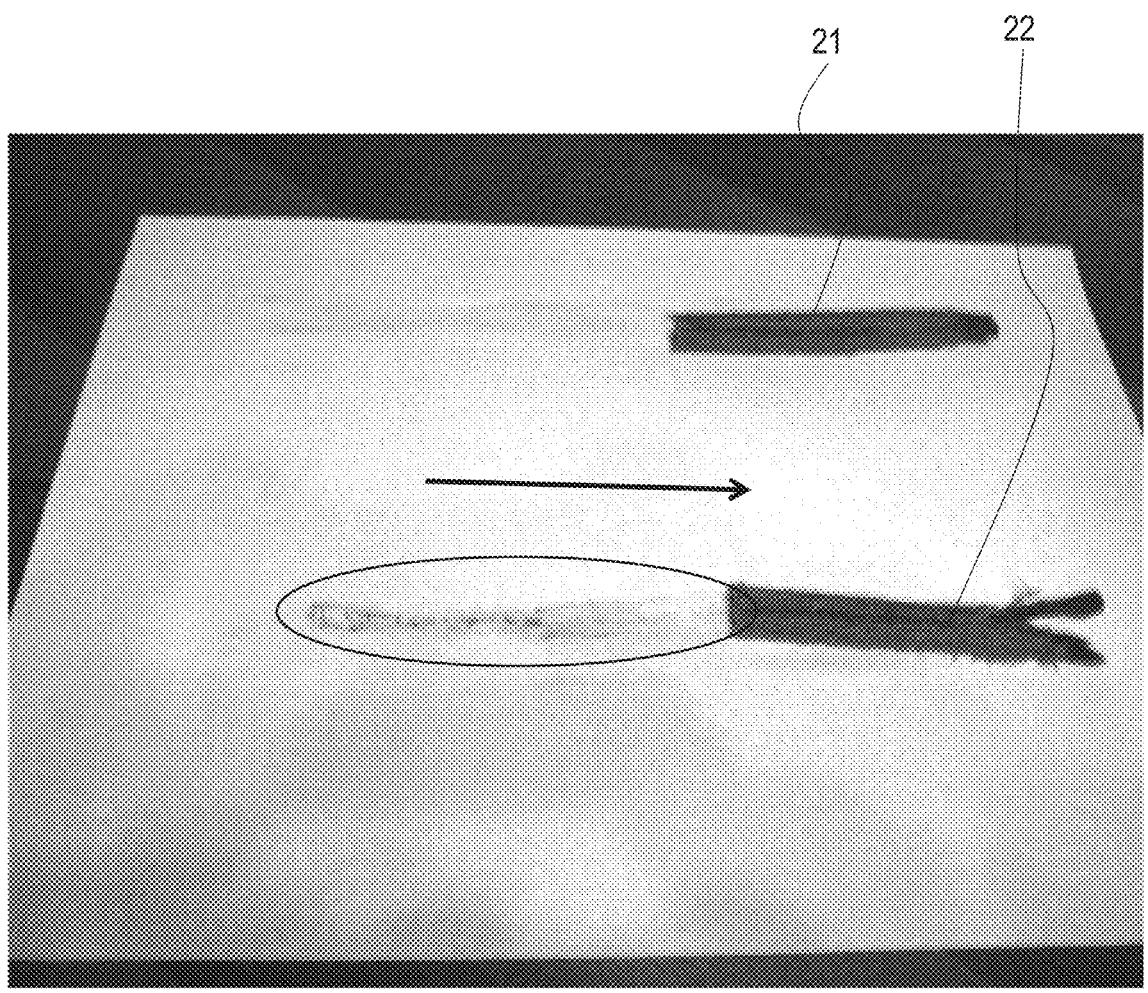
FIG. 12 is a view showing a photograph of residues in the hoses.

FIG. 12 is a view showing a photograph of residues in the hoses 21, 22. In order to confirm the presence of residue in the hoses 21 and 22, the hoses 21 and 22 are longitudinally incised, the inside of the hoses 21 and 22 are rubbed against white paper, and moved to the right side. The upper side in FIG. 12 is the hose 21 through which nanobubble water generated by the liquid processing nozzle 701 is passed, and the lower side is the hose 22 through which tap water is passed without using the liquid processing nozzle 701. The hose 21 through which the nanobubble water generated by the liquid processing nozzle 701 was passed had no residue at all. Black contamination residue was found in the hose 22 which was supplied with tap water without using the liquid processing nozzle 701.

1-4 Discussion

Based on the above results, the following considerations were made.

The adhesion of fungus such as black mold and biofilm caused by bacteria in used hoses was cultivated in a state where tap water containing chlorine as a fungicide was supplied until just before. It was confirmed anew that contamination in hoses was unavoidable only by tap water.

In the present experiment, it was confirmed that, while there was little effect of removing and cleaning once adhered contaminants only by passing tap water, there was a clear effect of removing and cleaning by passing 50 milliliters per minute of nanobubble water produced by the liquid processing nozzle 701.

Experiment 2

Experiment 2 is an experiment using nano paste.

2-1 Contents of Experiment

In order to quantitatively measure the peeling effect of the biofilm by the liquid processing nozzle 701, a pseudo-biofilm made of nano paste was attached to a transparent tube, and a visual comparison experiment was carried out.

2-2 Experimental Protocols

Figure 13A:
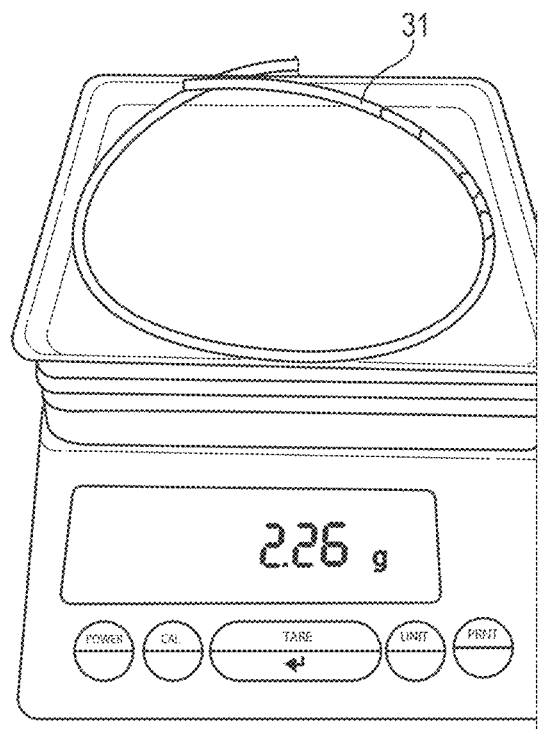
FIG. 13A is a view showing a photograph of a tube having a length of 50 cm and a weight of 2.26 g including a coating film.
Figure 13B:
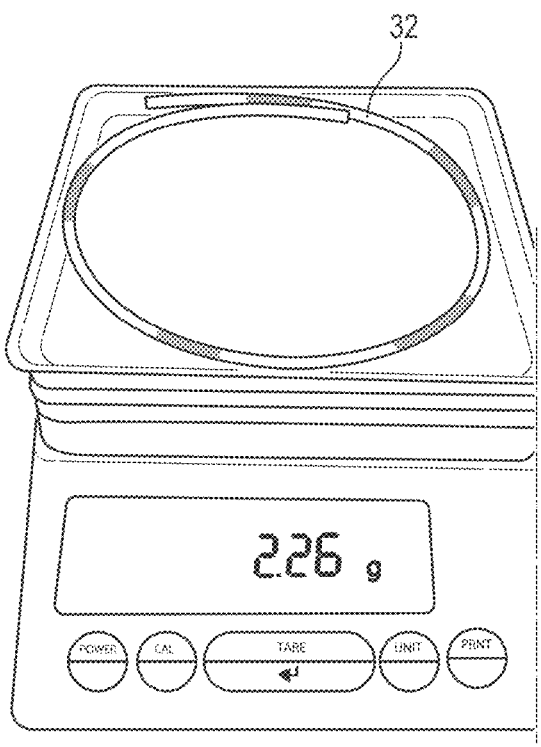
FIG. 13B is a view showing a photograph of a tube having a length of 50 cm and a weight of 2.26 g including a coating film.

The pseudo-biofilm (natto paste: 50%, polysaccharide: 50%, mixed, gelled) was encapsulated into two transparent vinyl tubes (tubes 31 and 32) (outside diameter: 2 mm, inside diameter: 1 mm, length: 50 cm). During semi-drying after 12 hours, a wire of 0.5 mm was passed through the tube 31 and the tube 32 to hollow out the center so that the inner walls of the tube 31 and the tube 32 were covered with the pseudo-biofilm. When the pseudo-biofilm was encapsulated into both the tube 31 and the tube 32, the weight was 2.85 g, and when dried after 72 hours, the weight was 2.26 g. FIG. 13A is a view showing a photograph of the tube 31 having the length of 50 cm and the weight of 2.26 g including the coating film. FIG. 13B is a view showing a photograph of the tube 32 having the length of 50 cm and the weight of 2.26 g including the coating film. The nanobubble water generated by the liquid processing nozzle 701 was passed through the tube 31 at a water temperature of 35° C. and a flow rate of 50 milliliters per minute. The tap water was supplied to the tube 32 at the water temperature of 35° C. and the flow rate of 50 milliliters per minute without using the liquid processing nozzle 701. The water flows to the tube 31 and the tube 32 were started simultaneously, and the film removing abilities in the tube 31 and the tube 32 were observed with the passage of time.

2-3 Experimental Results

Figure 14:
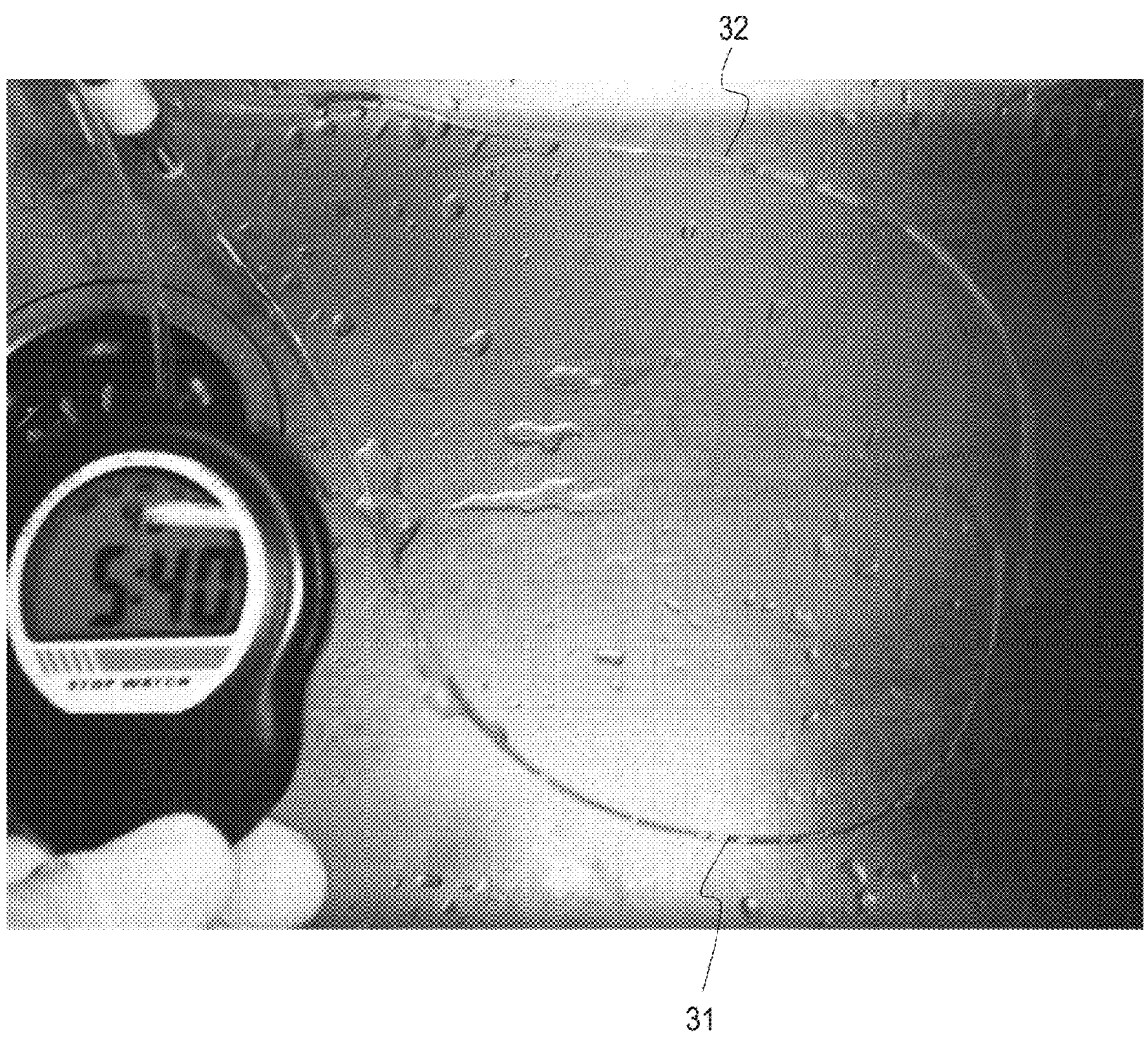
FIG. 14 is a view showing a photograph of tubes after 5 minutes from a start of water flow.

After 2 minutes from the start of water flow, a peeling of the coating film occurred in the tube 31 through which the nanobubble water produced by the liquid processing nozzle 701 was passed. FIG. 14 is a view showing a photograph of the tube 31 and the tube 32 after 5 minutes from the start of water flow. The lower tube is the tube 31. The upper tube is the tube 32. In a case that the liquid processing nozzle 701 was used, the coating film on the inner wall of the tube 31 was substantially removed after 5 minutes. In a case that the liquid processing nozzle 701 is not used, about 60% of the coating film on the inner wall of the tube 32 still remains after 5 minutes.

Figure 15A:
FIG. 15A is an enlarged view of a photograph of the tube after 6 minutes from the start of water flow.
Figure 15B:
FIG. 15B is an enlarged view of a photograph of the tube after 6 minutes from the start of water flow.
Figure 16:
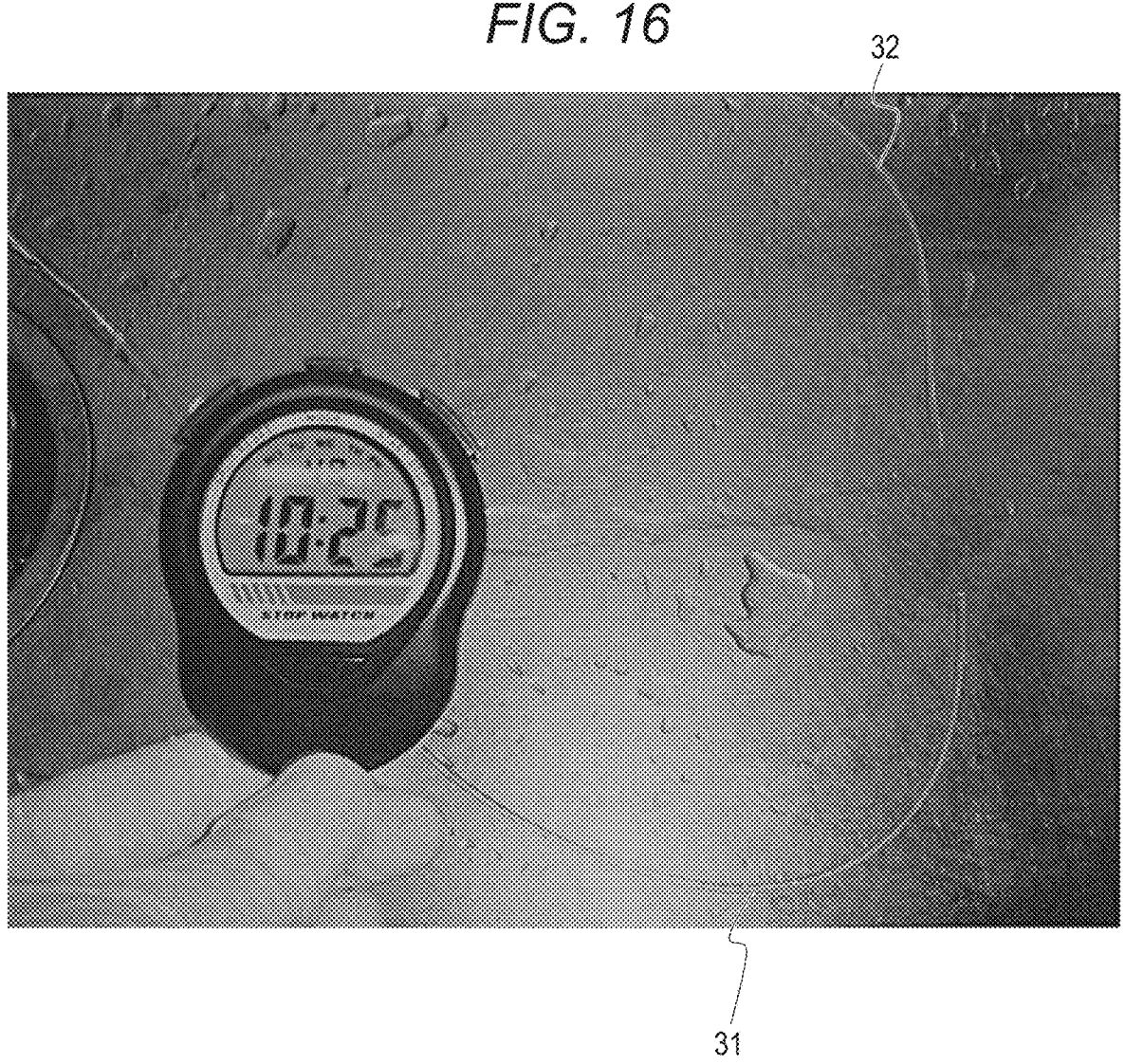
FIG. 16 is a view showing a photograph of the tubes after 10 minutes from the start of water flow.
Figure 17A:
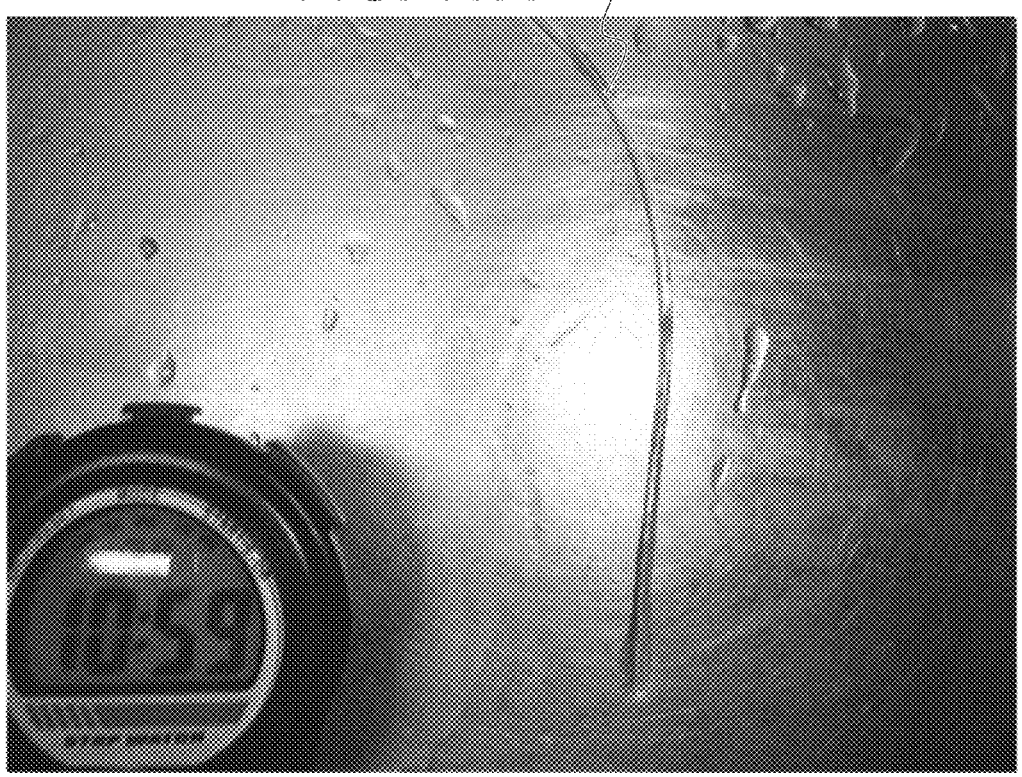
FIG. 17A is a view showing a photograph of the tube after 10 minutes from the start of water flow.
Figure 17B:
FIG. 17B is a view showing a photograph of the tube after 15 minutes from the start of water flow.

FIG. 15A is an enlarged view showing a photograph of the tube 31 after 6 minutes from the start of water flow. FIG. 15B is an enlarged view showing a photograph of the tube 32 after 6 minutes from the start of water flow. FIG. 16 is a view showing a photograph of the tube 31 and the tube 32 after 10 minutes from the start of water flow. The lower tube is the tube 31. The upper tube is the tube 32. After 10 minutes from the start of water flow, the water discharged from the tube 31 using the liquid processing nozzle 701 became visually transparent, and the biofilm was successfully removed. FIG. 17A and FIG. 17B are views showing photographs of the tube 32 not using the liquid processing nozzle 701 after 10 minutes and 15 minutes have elapsed from the start of water flow, respectively. FIG. 17A is the view showing the photograph of the tube 32 after 10 minutes from the start of water flow. FIG. 17B is the view showing the photograph of the tube 32 after 15 minutes from the start of water flow. Observation of the tube 32 without using the liquid processing nozzle 701 was continued from 10 minutes to 15 minutes after the start of water flow, but no change was observed in the remaining state of the coating film.

Figure 18:
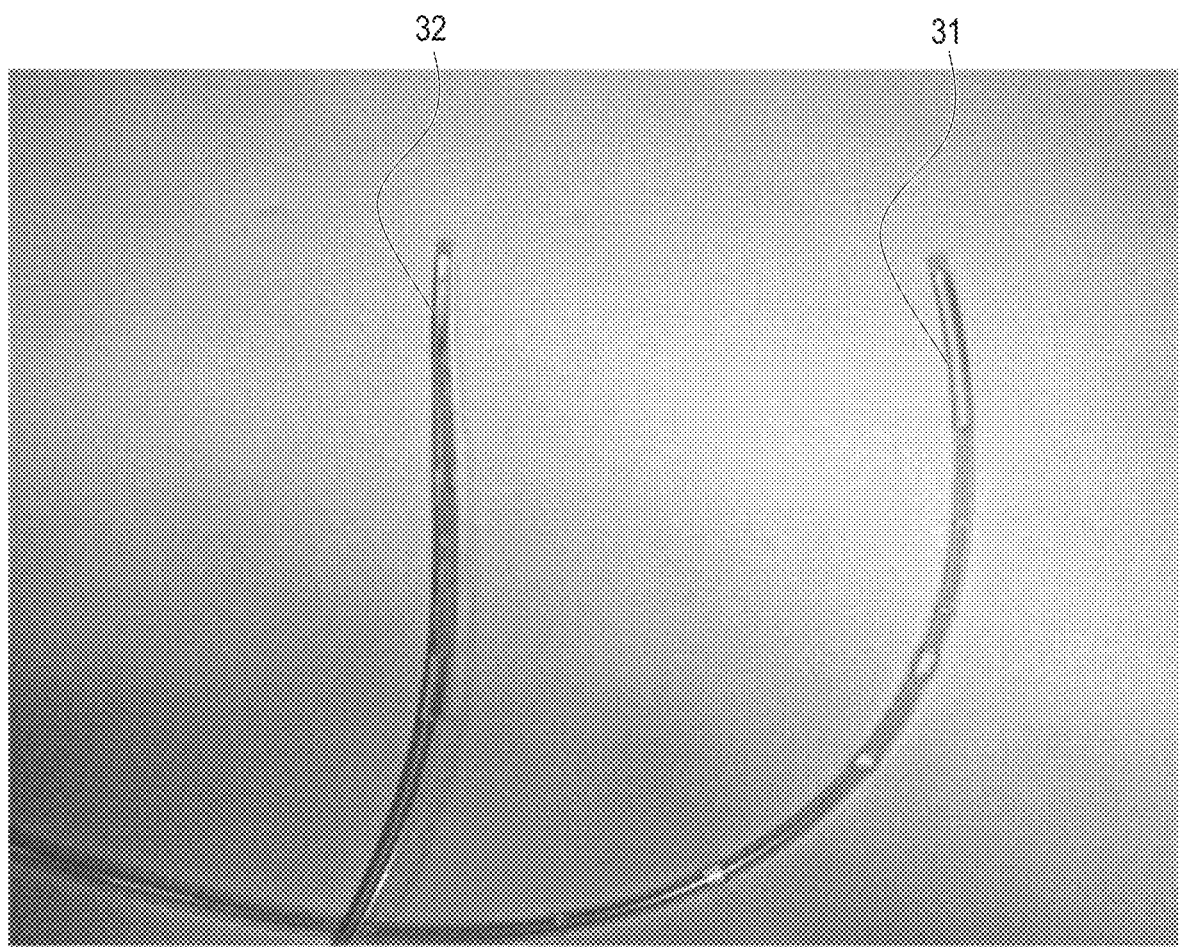
FIG. 18 is a view showing a photograph of the tubes after 20 minutes from the start of water flow.

FIG. 18 is a view showing a photograph of the tube 31 and the tube 32 after 20 minutes from the start of water flow. The tube on the left side in FIG. 18 is the tube 32 through which tap water is passed without using the liquid processing nozzle 701, and the tube on the right side is the tube 31 through which nanobubble water generated by the liquid processing nozzle 701 is passed. Even after 20 minutes had passed from the start of water flow, since there was no change in the remaining state of the coating film in the tube 32 (left side in FIG. 18) through which tap water was passed without using the liquid processing nozzle 701, water flow was temporarily stopped.

Figure 19:
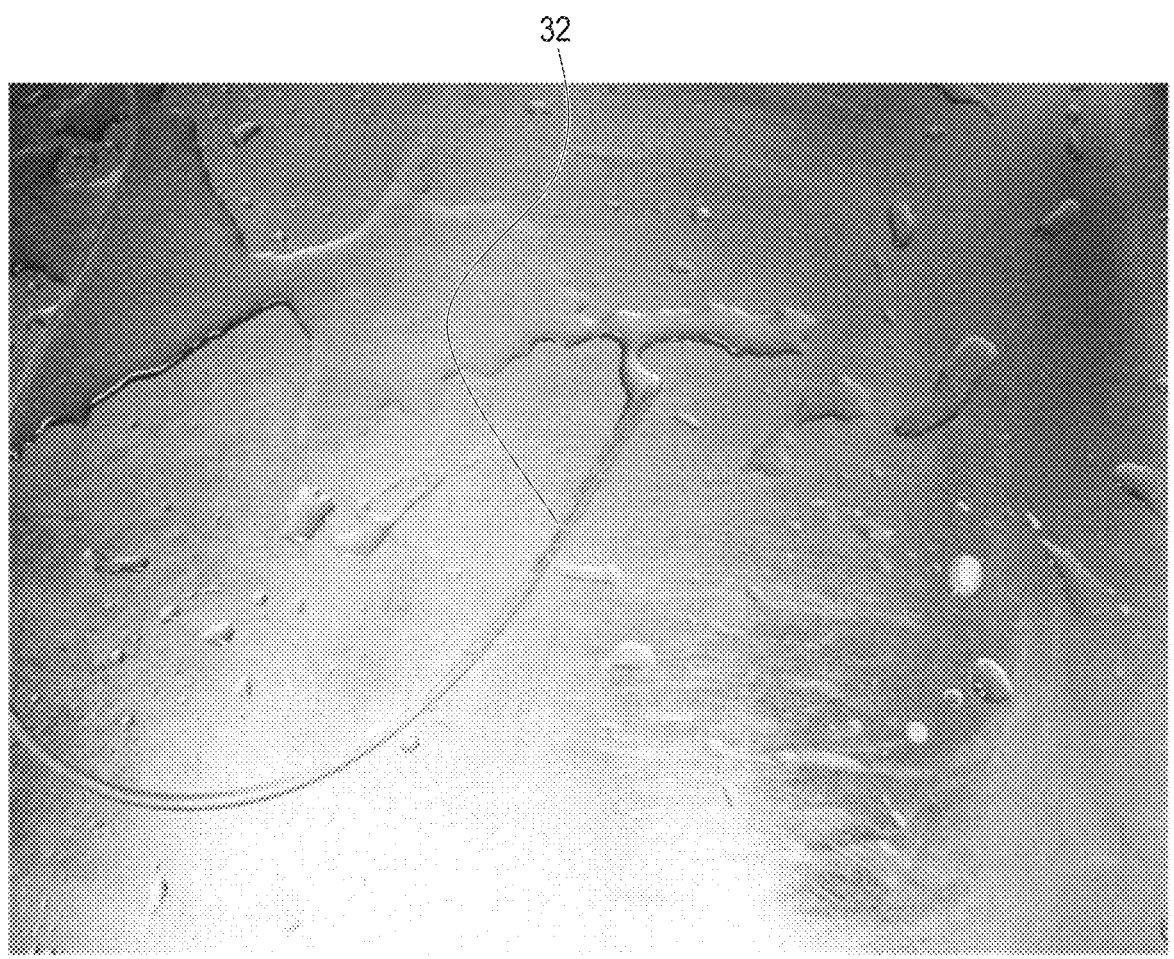
FIG. 19 is a view showing a photograph of the tube to which the liquid processing nozzle is connected and water is passed for 3 minutes.

Therefore, the liquid processing nozzle 701 was connected to the tube 32, and the nanobubble water produced by the liquid processing nozzle 701 was again passed through the tube 32. FIG. 19 is a view showing a photograph of the tube 32 to which the liquid processing nozzle 701 is connected and water is passed for 3 minutes. The coating film which could not be removed even after 20 minutes was elapsed in the case in which only tap water was passed without using the liquid processing nozzle 701 was completely removed by passing the nanobubble water generated by the liquid processing nozzle 701 for less than 3 minutes.

2-4 Discussion

Since the experimental condition is the ultra-low water flow rate as low as 50 milliliters per minute, an extremely thin tube with an inside diameter of 1 mm was used to fill the tube with tap water or nanobubble water. The amount of pseudo-biofilm used is also small, and the thickness of the coating film on the inner wall of the tube is estimated to be about 0.2 mm to 0.3 mm. In Experiment 2 as well, the liquid processing nozzle 701 exhibited the coating film peeling effect of a large difference compared with tap water even at an ultra-low water flow rate of 50 milliliters per minute. Further, when the liquid processing nozzle 701 was connected to the tube 32, of which a coating film was not able to be peeled off by passing tap water for 20 minutes, and the water was passed through the tube 32 through the liquid processing nozzle 701, the coating film which could not be removed by tap water could be removed in a short time. From this experiment, it is clear that the liquid processing nozzle 701 has the excellent effect of peeling off the biofilm, and it can be seen that sufficient nanobubble water is produced by the liquid processing nozzle 701.

From the above results, even in an actual dental clinic environment, by constantly connecting the liquid processing nozzle 701 to the water supply circuit of the scaler, the biofilm contamination in the water supply circuit can be suppressed, and the inside of the scaler can be maintained in a clean state.

Second Embodiment

The second embodiment will be described below. In the second embodiment, the same structure as in the first embodiment is denoted by the same reference numerals and description thereof is omitted. Since the dental unit 300 and the dental device 705 of the second embodiment are the same as those of the first embodiment, their descriptions are omitted. A liquid processing nozzle 801 of the second embodiment includes a plurality of sets in each of which four protrusions 10 are arranged in the cross shape surrounding the center axis O. The second embodiment will now be described with reference to FIG. 20, FIG. 21A, FIG. 21B, and FIG. 21C.

Figure 20:
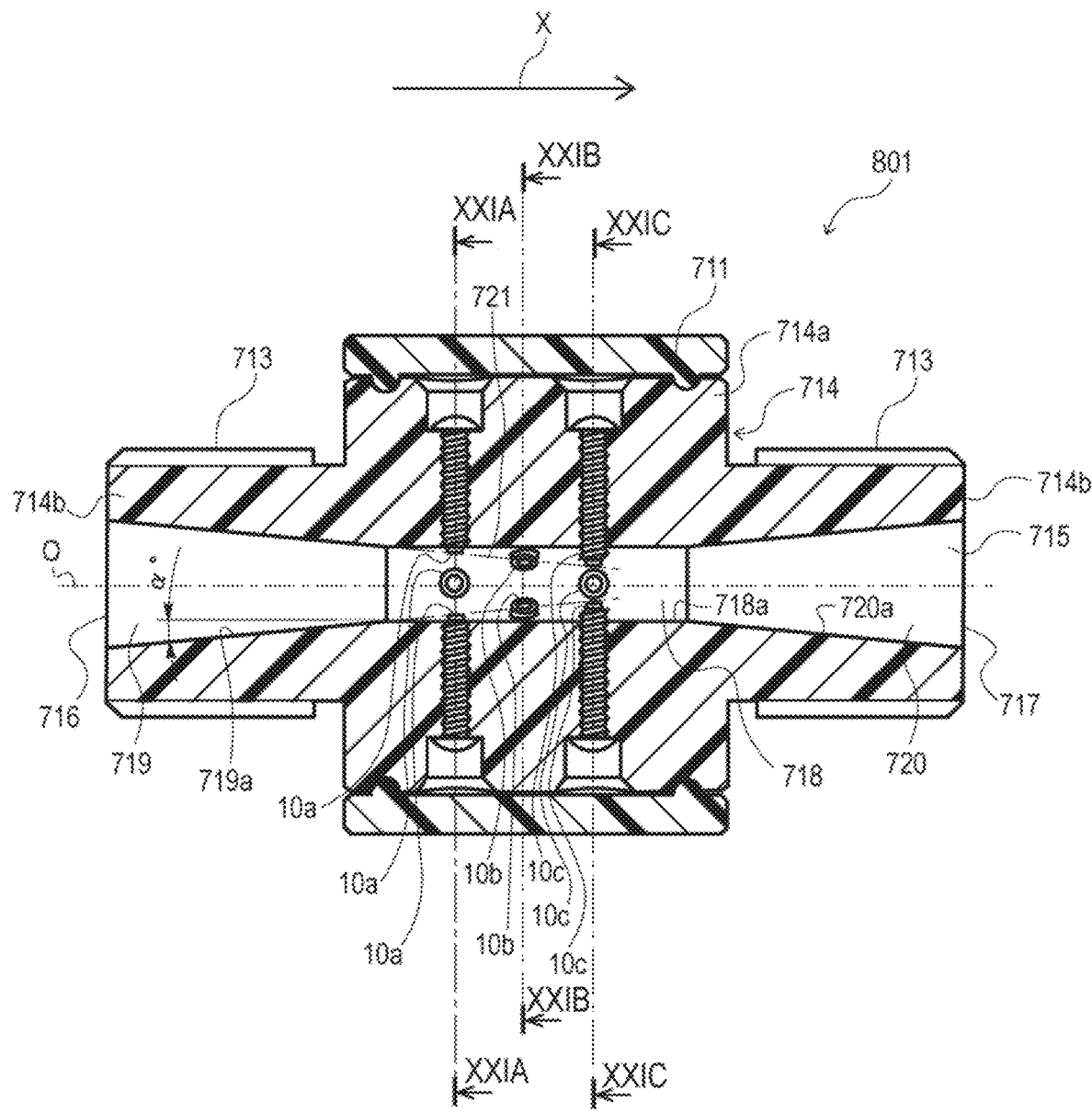
FIG. 20 is a cross-sectional view of a liquid processing nozzle of a second embodiment.
Figure 21A:
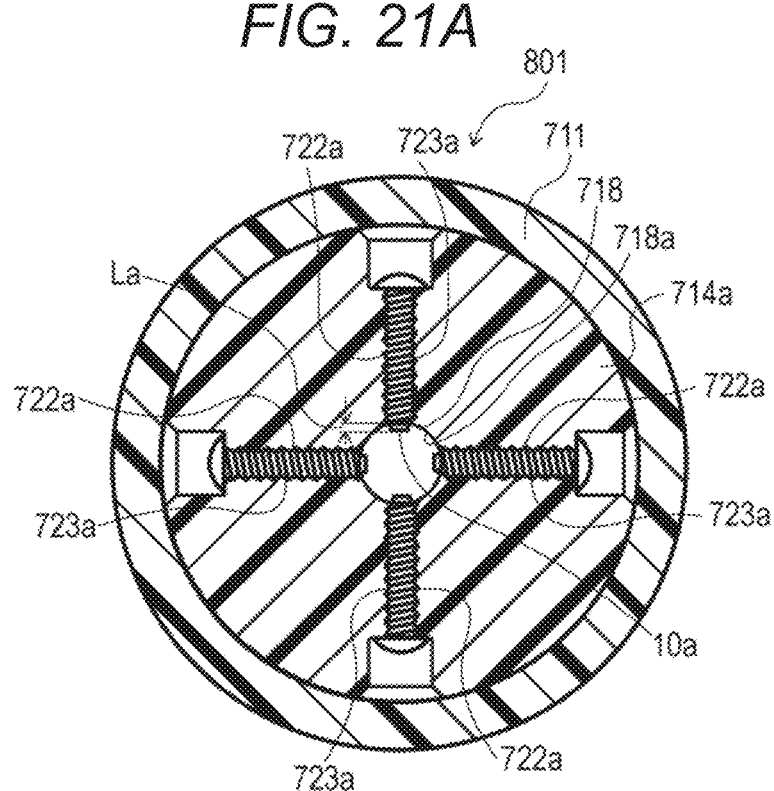
FIG. 21A is a cross-sectional view of the liquid processing nozzle taken along the lines XXIA-XXIA of FIG. 20.
Figure 21B:
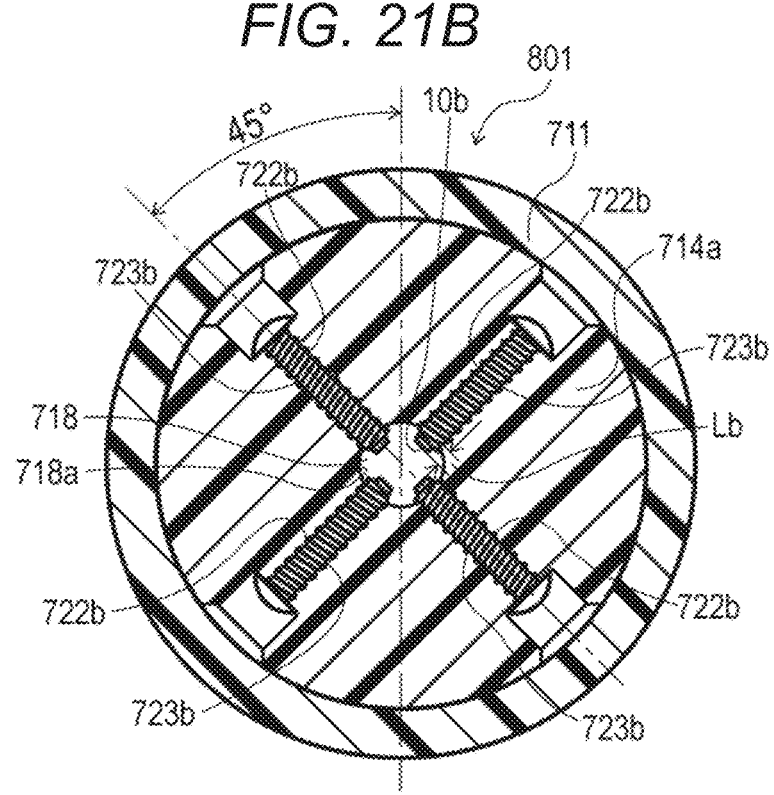
FIG. 21B is a cross-sectional view of the liquid processing nozzle taken along the lines XXIB-XXIB of FIG. 20.
Figure 21C:
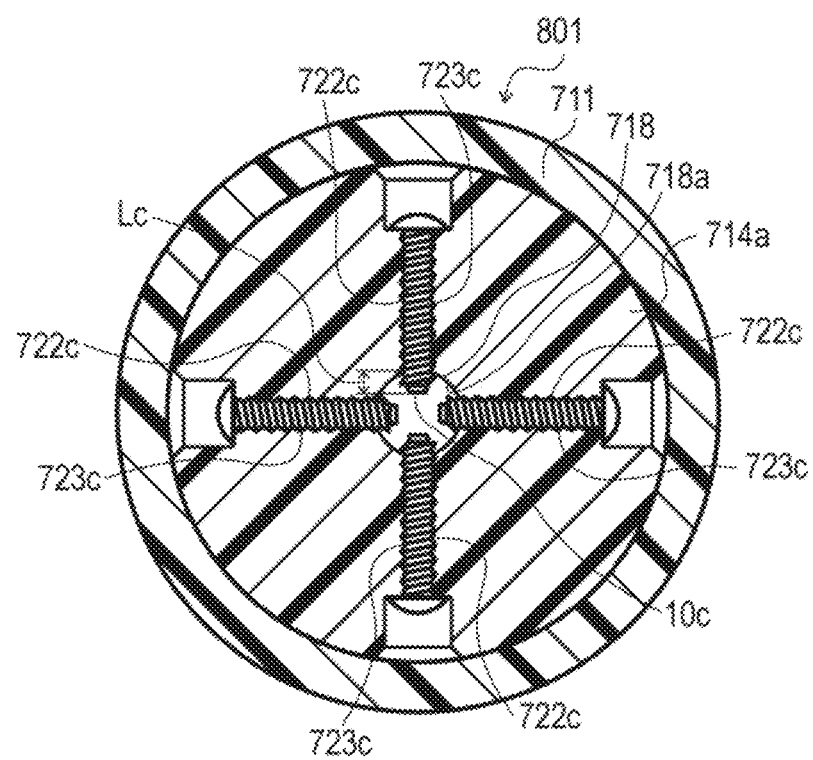
FIG. 21C is a cross-sectional view of the liquid processing nozzle taken along the lines XXIC-XXIC of FIG. 20.

FIG. 20 is a cross-sectional view of the liquid processing nozzle 801 of the second embodiment. FIG. 21A is a cross-sectional view of the liquid processing nozzle 801 taken along the lines XXIA-XXIA of FIG. 20. FIG. 21B is a cross-sectional view of the liquid processing nozzle 801 taken along the lines XXIB-XXIB of FIG. 20. FIG. 21C is a cross-sectional view of the liquid processing nozzle 801 taken along the lines XXIC-XXIC of FIG. 20. In FIG. 20, FIG. 21A, FIG. 21B, and FIG. 21C, structures similar to those of the first embodiment shown in FIG. 3, FIG. 4A, FIG. 4B, FIG. 4C, FIG. 4D, and FIG. 4E are denoted by the similar reference numerals, and description thereof will be omitted. As shown in FIG. 20, FIG. 21A, FIG. 21B, and FIG. 21C, the liquid processing nozzle 801 of the second embodiment is provided with only the screw members 723a, 723b, and 723c similar to those of the first embodiment, and the screw members 723d and 723e (type B) of the first embodiment are not provided. The liquid processing nozzle 801 of the second embodiment is provided with only the type (type A) in which the screw tips of the screw members 723a, 723b, and 723c face the center axis O in a cross section taken along the plane orthogonal to the center axis O of the liquid flow path 715. The distances La, Lb, and Lc by which the protrusions 10a, 10b, and 10c protrude from the inner surface 718a of the restriction hole 718 have the following relationship.

$$La < Lb < Lc$$

As the protrusions 10a, 10b, and 10c go from upstream to downstream in the liquid flow direction X, the distances La, Lb, and Lc protruding from the inner surface 718a of the restriction hole 718 gradually increase. In this way, the virtual curved surface connecting the most protruding portions of the protrusions 10a, 10b, and 10c is tapered from the upstream to the downstream in the liquid flow direction X. Thus, the flow velocity of the liquid passing through the restriction hole 718 is further increased, and the possibility of generating cavitation in the liquid by the protrusions 10a, 10b, and 10c can be enhanced.

In the embodiment, the three sets of protrusions 10a, 10b, and 10c are provided, but for example, only two sets of protrusions 10a and 10b may be provided, or four or more sets of protrusions may be provided.

According to the embodiment, even in a case that the liquid processing nozzle 801 is connected to the washing water hose 703 having the relatively small liquid flow rate, the formation of the biofilm in the washing water hose 703 can be suppressed.

Third Embodiment

The third embodiment will be described below. In the third embodiment, the same structures as those in the first embodiment is denoted by the same reference numerals and description thereof is omitted. Since the dental unit 300 and the dental device 705 of the third embodiment are the same as those of the first embodiment, their descriptions are omitted. A liquid processing nozzle 901 of the third embodiment includes a plurality of sets in which two protrusions 11 are disposed opposite to each other on both sides of the center axis O. The third embodiment will now be described with reference to FIG. 22, FIG. 23A, FIG. 23B, and FIG. 23C.

Figure 22:
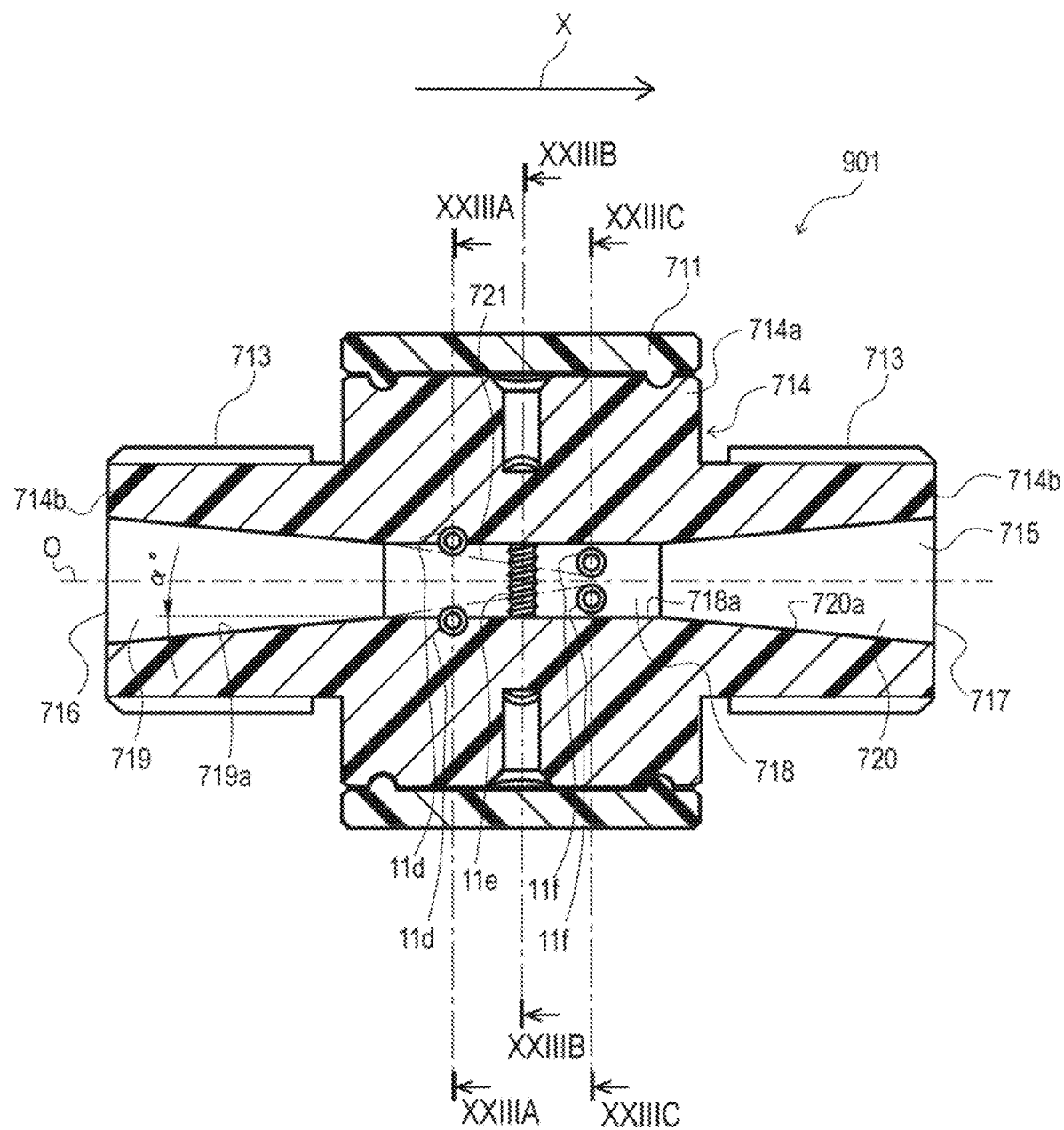
FIG. 22 is a cross-sectional view of a liquid processing nozzle of a third embodiment.
Figure 23A:
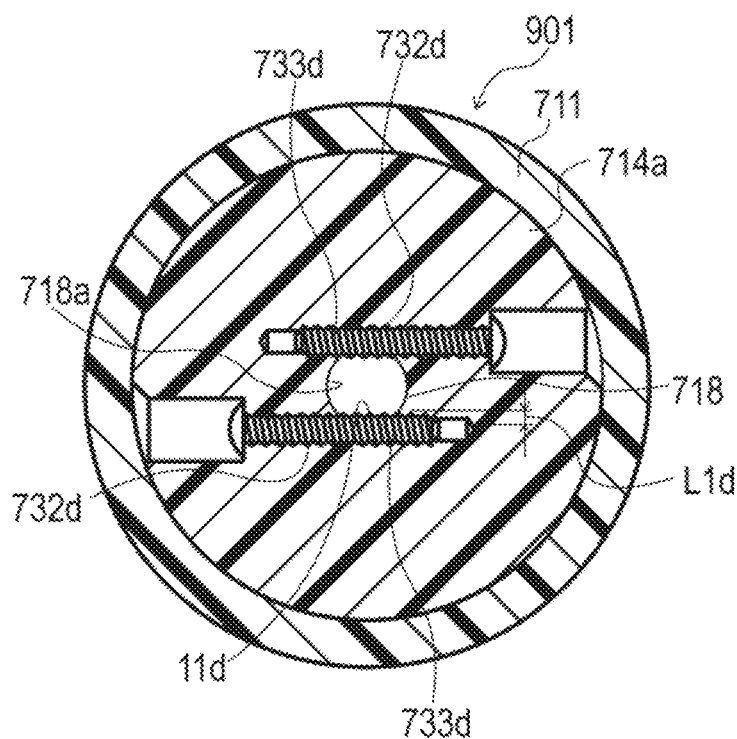
FIG. 23A is a cross-sectional view of the liquid processing nozzle taken along the lines XXIIIA-XXIIIA of FIG. 22.
Figure 23B:
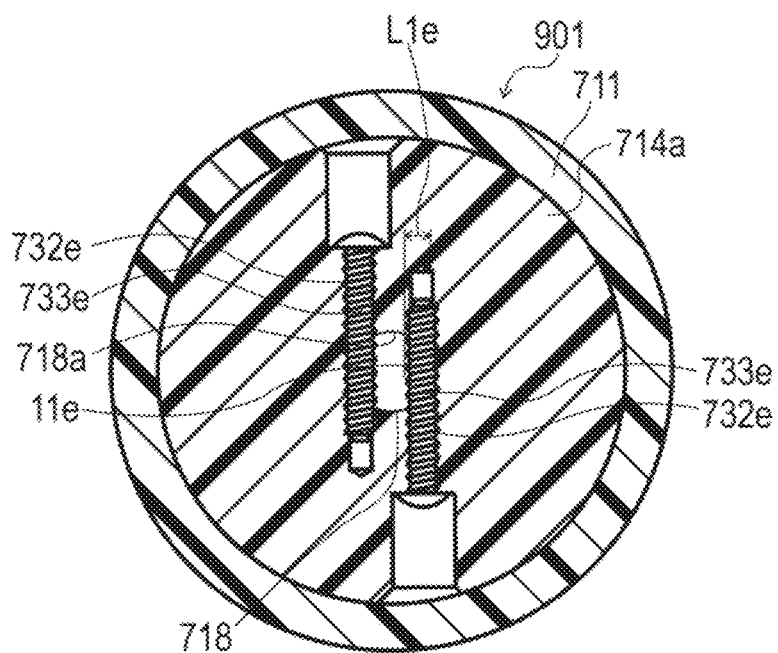
FIG. 23B is a cross-sectional view of the liquid processing nozzle taken along the lines XXIIIB-XXIIIB of FIG. 22.
Figure 23C:
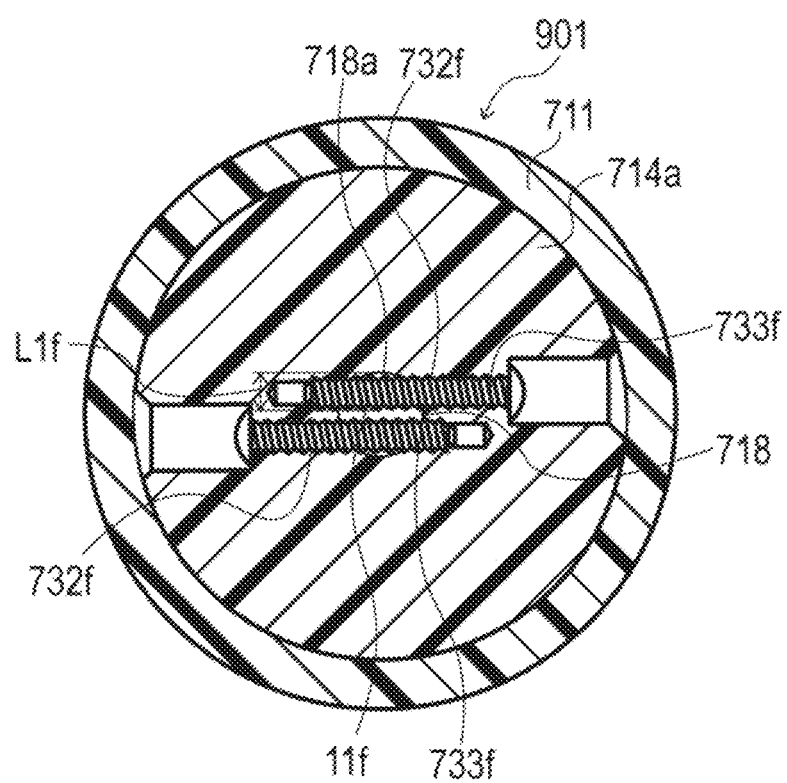
FIG. 23C is a cross-sectional view of the liquid processing nozzle taken along the lines XXIIIC-XXIIIC of FIG. 22.

FIG. 22 is a cross-sectional view of the liquid processing nozzle 901 of the third embodiment. FIG. 23A is a cross-sectional view of the liquid processing nozzle 901 taken along the lines XXIIIA-XXIIIA of FIG. 22. FIG. 23B is a cross-sectional view of the liquid processing nozzle 901 taken along the lines XXIIIB-XXIIIB of FIG. 22. FIG. 23C is a cross-sectional view of the liquid processing nozzle 901 taken along the lines XXIIIC-XXIIIC of FIG. 22. In FIG. 22, FIG. 23A, FIG. 23B, and FIG. 23C, structures similar to those of the first embodiment shown in FIG. 3, FIG. 4A, FIG. 4B, FIG. 4C, FIG. 4D, and FIG. 4E are denoted by similar reference numerals, and description thereof will be omitted. As shown in FIG. 22, FIG. 23A, FIG. 23B, and FIG. 23C, the liquid processing nozzle 901 of the third embodiment is provided with screw members 733d, 733e and 733f similar to the screw members 723d and 723e of the first embodiment. The liquid processing nozzle 901 of the third embodiment is provided with only the type (type B) in which the screw shaft parts of the screw members 733d, 733e, and 733f are closest to the center axis O. In the third embodiment, the screw members 723a, 723b, and 723c (type A) of the first embodiment are not provided.

In the large diameter portion 714a, two screw holes 732d penetrating from the outer peripheral surface of the large diameter portion 714a to the restriction hole 718 are formed in opposite directions. At a position rotated approximately 90 degrees with respect to the two screw holes 732d, two screw holes 732e penetrating from the outer peripheral surface of the large diameter portion 714a to the restriction hole 718 are formed in the opposite directions in the large diameter portion 714a. Similarly, at a position rotated approximately 90 degrees with respect to the two screw holes 732e, two screw holes 732f penetrating from the outer peripheral surface of the large diameter portion 714a to the restriction hole 718 are formed in the opposite directions in the large diameter portion 714a. The three sets of screw members 733d, 733e, and 733f are screwed into the three sets of screw holes 732d, 732e, and 732e, respectively.

The most protruding portions of the screw members 733d, 733e, and 733f protruding from the inner surface 718a of the restriction hole 718 are not the tip ends of the screw members 733d, 733e, and 733f but the screw shaft parts. A liquid flow gap is formed between two parallel screw parts 733. The most protruding portions of the screw shaft parts of the screw members 733d, 733e, and 733f constitute the protrusions 11d, 11e, and 11f. The distances (protrusion amounts) L1d, L1e, and L1f by which the protrusions 11d, 11e, and 11f protrude from the inner surface 718a of the restriction hole 718 have the following relationship.

$$L1d < L1e < L1f$$

As the protrusions 11d, 11e, and 11f go from upstream to downstream in the liquid flow direction X, the distances L1d, L1e, and L1f protruding from the inner surface 718a of the restriction hole 718 gradually increase. In this way, the virtual curved surface connecting the most protruding portions of the protrusions 11d, 11e, and 11f is tapered from the upstream to the downstream in the liquid flow direction X. Thus, the flow velocity of the liquid passing through the restriction hole 718 is further increased, and the possibility of generating cavitation in the liquid by the protrusions 11d, 11e, and 1 if can be increased.

In the embodiment, the three sets of protrusions 11d, 11e, and 11f are provided, but for example, only two sets of protrusions 11d and 11e may be provided, or four or more sets of protrusions may be provided. When the restriction hole 718 is peeked out, it is preferable that two sets of protrusions 11d and 11e are arranged in parallel crosses.

According to the embodiment, even in a case that the liquid processing nozzle 901 is connected to the washing water hose 703 having the relatively small liquid flow rate, the formation of the biofilm in the washing water hose 703 can be suppressed.

The liquid processing nozzles 701, 801, and 901 of the first embodiment to the third embodiment can be attached to the liquid piping having the inside diameter of about 3 mm to 5 mm having the relatively small liquid flow rate. However, the liquid processing nozzles 701, 801, and 901 can have the same effect even when their sizes are increased. Therefore, the liquid processing nozzles 701, 801, and 901 of the first embodiment to the third embodiment can also be attached to a liquid piping having an inside diameter of 6 mm or more, for example, from 10 mm to 15 mm. That is, the liquid processing nozzles 701, 801, and 901 can also be attached to the washing water main piping 540 between the water supply source piping 431 and the dental unit 300. The liquid processing nozzles 701, 801, and 901 can also be attached to the water supply tube 502 having an inside diameter of about 2 mm for supplying liquid to the handpiece 421 of the dental unit 300.

This application claims the benefit of Japanese Patent Application No. 2019-190685, filed on Oct. 18, 2019, which is hereby incorporated by reference herein its entirety.

REFERENCE SIGNS LIST

431 . . . water supply source piping
421, 706 . . . handpiece
703 . . . liquid piping
701, 801, 901 . . . liquid processing nozzle
716 . . . liquid inlet
717 . . . liquid outlet
715 . . . liquid flow path
714 . . . nozzle body
10a, 10b, 10c, 10d, 10e, 11d, 11e, 11f . . . protrusion
La, Lb, Lc, Ld, Le, L1d, L1e, L1f . . . distance (protrusion amount)
X . . . flow direction

The invention claimed is:

1. A liquid processing nozzle to be connected to a liquid piping between a handpiece and a water supply source piping, the liquid processing nozzle comprising:
a nozzle body in which a liquid inlet, a liquid outlet, and a liquid flow path communicating the liquid inlet and the liquid outlet are formed; and
a plurality of protrusions protruding from an inner surface of the liquid flow path into the liquid flow path,
wherein the plurality of protrusions are arranged so that protrusion amounts of the plurality of protrusions protruding from the inner surface of the liquid flow path into the liquid flow path gradually increase as they go from an upstream side to a downstream side of the liquid flow path in a flow direction of a liquid from the liquid inlet to the liquid outlet.

2. The liquid processing nozzle according to claim 1, wherein a most protruding portion of each of the plurality of protrusions is located on a virtual tapered surface extending from the liquid inlet to the downstream side in the flow direction.

3. The liquid processing nozzle according to claim 1, wherein the liquid flow path includes a restriction hole having a cross-sectional area smaller than an area of the liquid inlet, and a tapered surface connecting the liquid inlet and the restriction hole, wherein the plurality of protrusions are provided in the restriction hole; and wherein a most protruding portion of each of the plurality of protrusions is located on a virtual extension surface extending from the tapered surface in the flow direction.

4. The liquid processing nozzle according to claim 1, wherein each of the plurality of protrusions has a ridge part and a groove part.

5. The liquid processing nozzle according to claim 1, wherein the plurality of protrusions include a plurality of screw members.

6. The liquid processing nozzle according to claim 5, wherein the plurality of screw members include a first set and a second set each comprising a plurality of screw members arranged so that screw tips of the plurality of members are directed to a center axis of the liquid flow path, wherein the first set is arranged upstream of the second set in the flow direction, and wherein a distance from the inner surface of the liquid flow path to the screw tips of the plurality of screw members of the second set is greater than a distance from the inner surface of the liquid flow path to the screw tips of the plurality of screw members of the first set.

7. The liquid processing nozzle according to claim 6, wherein the first set and the second set each is arranged in a cross shape in which four screw members surround the center axis, and wherein a liquid flow gap is formed at a center position of the cross shape formed by the four screw members.

8. The liquid processing nozzle according to claim 7, wherein the cross shape of the first set and the cross shape of the second set are offset from each other by approximately 45 degrees.

9. The liquid processing nozzle according to claim 5, wherein the plurality of screw members include a first set and a second set each comprising a plurality of screw members arranged so that screw shaft parts of the plurality of screw members are parallel to each other across a center axis of the liquid flow path, wherein the first set is arranged upstream of the second set in the flow direction, and wherein a distance from the inner surface of the liquid flow path to most protruding portions of the screw shaft parts of the plurality of screw members of the second set is greater than a distance from the inner surface of the liquid flow path to most protruding portions of the screw shaft parts of the plurality of screw members of the first set.

10. The liquid processing nozzle according to claim 9, wherein each of the first set and the second set has two screw members arranged in parallel across the center axis, and wherein a liquid flow gap is formed between the two screw members.

11. The liquid processing nozzle according to claim 10, wherein the two screw members of the first set and the two screw members of the second set are offset from each other by approximately 90 degrees.

12. The liquid processing nozzle according to claim 5, wherein the plurality of screw members include a first set comprising a plurality of screw members arranged so that screw tips of the plurality of screw members are directed to a center axis of the liquid flow path, and a second set comprising a plurality of screw members arranged so that screw shaft parts of the plurality of screw members are parallel to each other across the center axis, wherein the first set is arranged upstream of the second set in the flow direction, and wherein a distance from the inner surface of the liquid flow path to most protruding portions of the screw shaft parts of the plurality of screw members of the second set is greater than a distance from the inner surface of the liquid flow path to the screw tips of the plurality of screw members of the first set.

13. The liquid processing nozzle according to claim 12, wherein the first set is arranged in a cross shape in which four screw members surround the center axis, wherein a liquid flow gap is formed at a center position of the cross shape formed by the four screw members, wherein the second set has two screw members arranged in parallel across the center axis, and wherein a liquid flow gap is formed between the two screw members.

14. The liquid processing nozzle according to claim 5, wherein the plurality of screw members include a first set comprising a plurality of screw members arranged so that screw tips of the plurality of screw members are directed to a center axis of the liquid flow path, and a second set comprising a plurality of screw members arranged so that screw shaft parts of the plurality of screw members are parallel to each other across the center axis, wherein the second set is arranged upstream of the first set in the flow direction, and wherein a distance from the inner surface of the liquid flow path to the screw tips of the plurality of screw members of the first set is greater than a distance from the inner surface of the liquid flow path to most protruding portions of the screw shaft parts of the plurality of screw members of the second set.

15. The liquid processing nozzle according to claim 1, wherein the handpiece is provided to a dental device connected to a dental unit, and wherein the liquid processing nozzle is removably connected to a liquid piping connecting the dental device and the water supply source piping or a liquid piping connecting the dental device and the dental unit.

16. The liquid processing nozzle according to claim 15, wherein both ends of the liquid processing nozzle are removably attached to the liquid piping by union joints.

17. The liquid processing nozzle according to claim 16, wherein a filter is attached to a union joint upstream of the liquid processing nozzle in the flow direction.

18. The liquid processing nozzle according to claim 1, wherein the liquid processing nozzle is removably connected to a liquid piping between the water supply source piping and a dental unit.

19. The liquid processing nozzle according to claim 1, wherein the handpiece comprises at least one of an engine handpiece, an ultrasonic scaler handpiece, a three-way syringe and an air turbine handpiece.

20. The liquid processing nozzle according to claim 1, wherein the plurality of protrusions have a cylindrical shape or a polygonal shape.

* * * * *